(12) United States Patent
Bosio et al.

(10) Patent No.: US 11,529,312 B2
(45) Date of Patent: Dec. 20, 2022

(54) *FRANCISELLA* LIPIDS AS BROAD ANTI-INFLAMMATORY THERAPEUTICS AND

(51) Int. Cl.
| | |
|---|---|
| *C12N 1/20* | (2006.01) |
| *A61K 31/6615* | (2006.01) |
| *A61P 11/00* | (2006.01) |
| *A61P 29/00* | (2006.01) |
| *A61K 31/685* | (2006.01) |
| *A61K 39/00* | (2006.01) |

(52) U.S. Cl.
CPC .......... *A61K 39/0208* (2013.01); *A61P 11/00* (2018.01); *A61P 29/00* (2018.01); *C12N 1/20* (2013.01); *A61K 2039/55555* (2013.01); *A61K 2039/58* (2013.01)

(58) Field of Classification Search
CPC . A61K 2039/55555; C12N 1/20; A61P 29/00; A61P 11/00
See application file for complete search history.

(56) References Cited

U.S. PATENT DOCUMENTS

| | | | | |
|---|---|---|---|---|
| 2007/0014842 | A1* | 1/2007 | Martin | A61K 9/127 424/450 |
| 2007/0042004 | A1* | 2/2007 | Vogel | A61K 31/739 424/234.1 |
| 2008/0248094 | A1* | 10/2008 | Sprott | A61K 39/39 424/450 |
| 2010/0166840 | A1* | 7/2010 | Atthachai | A61K 9/127 424/450 |
| 2012/0135067 | A1* | 5/2012 | Matsuda | A61K 39/39 424/450 |
| 2015/0157570 | A1 | 6/2015 | Babiychuk et al. | |
| 2015/0283133 | A1 | 10/2015 | Gonda et al. | |

OTHER PUBLICATIONS

Bosio et al., "Identification of a Unique Lipid from *Francisella tularensis* as an Effective Therapeutic for Viral Medicated Inflammation," *J. Immunol.*, vol. 196 (1 Supplement: 76.24, 2016.

Ireland et al., "*Francisella tularensis* SchuS4 and SchuS4 Lipids Inhibit IL-12p40 in Primary Human Dendritic Cells by Inhibition of IRF1 and IRF8," *J. Immunol.*, vol. 191:1276-1286, 2013.

Ireland et al., "Unique *Francisella* Phosphatidylethanolamine Acts as a Potent Anti-Inflammatory Lipid," *J Innate Immun* 10:291-305, 2018.

Ichimori et al., "Barotropic Phase Transitions and Pressure-Induced Interdigitation on Bilayer Membranes of Phospholipids with Varying Acyl Chain Lengths," *Biochim. Biophys. Acta.*, vol. 1414:165-174, 1998.

Kučerka et al., "What Determines the Thickness of a Biological Membrane," *Gen. Physiol. Biophys.*, vol. 28:117-125, 2009.

Mansilla et al., "Control of Membrane Lipid Fluidity by Molecular Thermosensors," *J. Bacteriol.*, vol. 186:6681-6688, 2004.

Matsuki et al., "Thermotropic and Barotropic Phase Transitions in Bilayer Membranes of Ether-Linked Phospholipids with Varying Alkyl Chain Lengths," *Biochim. Biophys. Acta*, vol. 1768: 479-489, 2007.

Nicolson, "The Fluid-Mosaic Model of Membrane Structure: Still relevant to understanding the structure, function and dynamics of biological membranes after more than 40 years," *Biochim. Biophys. Acta*, vol. 1838:1451-1466, 2014.

Russell N.J. (1984) The Regulation of Membrane Fluidity in Bacteria by Acyl Chain Length Changes. In: Kates M., Manson L.A. (eds) Membrane Fluidity. Biomembranes, vol. 12. Springer, Boston, MA. https://doi.org/10.1007/978-1-4684-4667-8_10.

* cited by examiner

FRANCISELLA LIPIDS AS BROAD ANTI-INFLAMMATORY THERAPEUTICS AND ASSOCIATED METHODS OF USE

CROSS-REFERENCE TO RELATED APPLICATIONS

This application is the U.S. National Stage of International Application No. PCT/US2017/026467, filed Apr. 6, 2017, which was published in English under PCT Article 21(2), which claims priority to U.S. Provisional Application No. 62/319,692, filed 7 Apr. 2016, entitled FRANCISELLA LIPIDS AS BROAD ANTI-INFLAMMATORY THERAPEUTICS AND ASSOCIATED METHODS OF USE, which is incorporated herein by reference in its entirety for all purposes.

GOVERNMENT FUNDING

Research supporting this application was carried out by the United States of America as represented by the Secretary, Department of Health and Human Services.

INCORPORATION BY REFERENCE

All documents cited or referenced herein, together with any manufacturer's instructions, descriptions, product specifications, and product sheets for any products mentioned herein or in any document incorporated herein by reference, and may be employed in the practice of the invention.

BACKGROUND

1. Field of the Invention

The present disclosure relates generally to the field of anti-inflammatories and to methods and compositions for treating and/or preventing inflammation related diseases and disorders, including viral and bacterial infections. In particular, the present disclosure relates to a therapeutic or pharmaceutical composition/agent effective to ameliorate pro-inflammatory responses, while not disrupting the immune system's ability to produce adaptive (i.e., acquired) immune responses.

2. Background

Anti-inflammatories, especially those used during viral infection, often have a deleterious side effect of greatly inhibiting the overall immune response, thereby disrupting the induction of adaptive immune responses (e.g., B cell and T cell activation). As a result, patients taking anti-inflammatories are plagued with the induction of poor immunity to pathogens, which can results in a failure to clear and/or control infections.

Interestingly, infections with certain subspecies (ssp.) of Francisella tularensis have been shown to induce an anti-inflammatory response/environment. Francisella tularensis is a highly infectious. Gram-negative, rod-shaped, coccobacillus aerobe bacterium. F. tularensis is a non-spore forming, non-motile, facultative intracellular bacterium with four major subspecies that are capable of infecting and proliferating in a variety of host cell types (including hepatocytes, endothelial cells, fibroblasts and mononuclear phagocytes). F. tularensis is a widespread zoonosis that affects humans, causing the fatal disease tularemia (also known as "rabbit fever"). F. tularensis ssp. novicida and spp. mediasiatica are generally considered attenuated for humans. F. tularensis ssp. holarctica (Type B; F. holarctica) causes serious disease in humans, but is not typically fatal. F. tularensis ssp. tularensis (Type A; F. tularensis) is highly infectious and can cause a lethal infection (mortality rate of approximately 30% when untreated) following inhalation of as few as 10 organisms in both humans and rodent models. Type A strains are geographically distributed in North America, while Type B strains are found throughout the northern hemisphere.

Human cases of tularemia usually result from a bite from a vector such as biting flies, ticks, and mosquitoes that have recently fed on an infected animal. There have been reported cases, however, of infections cause by contact with the dead, animals, infectious aerosols, and ingestion of contaminated food and water. Hunters, veterinarians, walkers and farmers are at the greatest risk of contracting tularemia because they are likely to come into contact with infected animals. The incidence of tularemia in humans is usually low, but an increase in the number of cases is observed when there is an epidemic in the local animal reservoir.

In vitro and in vivo studies have demonstrated that infection with virulent F. tularensis ssp. tularensis does not induce the pro-inflammatory response that attenuated strains of F. tularensis ssp. tularensis and subspecies of Francisella do. It has been shown that lipids isolated from virulent F. tularensis strain SchuS4 inhibit innate immune responses, e.g. the inflammatory response (Robin Ireland, et al. Francisella tularensis SchuS4 and SchuS4 Lipids Inhibit IL-12p40 in Primary Human Dendritic Cells by Inhibition of IRF1 and IRF8. J Immunol. 2013; 191: 1276-1286). Furthermore, this inhibition of the innate immune response is not observed with the attenuated live vaccine strain (LVS) isolated lipids. Id.

Moreover, when inflammatory responses are present during a Francisella infections, it has been shown to not be effective at controlling or clearing the bacterial infection, and in some cases, has contributes to morbidity and may contribute to the death of the infected individual. F. tularensis ssp. tularensis has been used as a biological weapon because of its highly infectious nature and ability to cause severe disease. The LVS is no longer licensed for use against tularemia, and antibiotic treatment of F. tularensis infected individuals does not always result in complete clearance of the infection.

Accordingly, there exists in the art an ongoing need for improved methods of treating or preventing infectious diseases and inflammatory diseases and disorders.

SUMMARY

As described below, the present disclosure features compositions and uses thereof for the treatment or prevention of a pathogen infection, inflammation, or a disease or disorder associated with inflammation. In particular, it was surprisingly and unexpectedly discovered that effective amounts of purified lipid from Francisella, for example Francisella tularensis, is efficacious as an anti-inflammatory.

Thus, in an aspect, the present disclosure provides an anti-inflammatory composition comprising an effective amount of purified lipid from Francisella, for example Francisella tularensis. In some embodiments, the Francisella tularensis is a virulent Francisella tularensis strain, e.g. Francisella tularensis ssp. tularensis. In another embodiment, the purified lipid comprises a phosphatidylethanolamine (PE), e.g. a PE having an acyl chain with a length in a range of from 5 to 13 or from 20 to 28 carbons. In an embodiment, the purified lipid is enriched for the PE.

In a particular embodiment, the purified lipid is PE, for example, a PE having two acyl chains wherein at least one acyl chain has a length of from 20 to 28 carbons. In a particular embodiment, the purified lipid is PE, for example, a PE having two acyl chains wherein at least one acyl chain has a length of from 5 to 13 carbons. In certain embodiments, the purified lipid is PE having two acyl chains, wherein one chain is from 5 to 13 carbons, and the other chain is in the range of from 20 to 28 carbons.

In certain embodiments, the composition further comprises phosphatidylcholine (PC), e.g., in effective amounts. In a particular embodiment, the ratio of PE:PC is in a range of from about 50:50 to about 95:5. In a further embodiment, the composition further comprises cholesterol. In some embodiments, the composition further comprises about 5% to about 20% cholesterol. In other embodiments, the PEPC composition comprises about 5% to about 20% cholesterol.

In another embodiment, the composition further comprises another purified lipid from *Francisella*. In a further embodiment, the another purified lipid is from *F. tularensis*, which can be a virulent strain of *F. tularensis*, for example ssp. *tularensis*. In a particular embodiment, the another purified lipid has anti-inflammatory properties, i.e. inhibits inflammation.

In other embodiments, the composition is a liposome, e.g. an emulsified liposome, comprising an effective amount of PE from *Francisella*, e.g., *Francisella tularensis*., as described herein. In certain embodiments, the liposome can have a diameter in a range of from about 20 nm to about 1,500 nm. In additional embodiments, the liposome comprises about 5% to about 20% cholesterol. Cholesterol further stabilizes the liposomes.

In any of the aspects or embodiments described herein, a liposome composition as described herein may further comprises phosphatidylcholine (PC), e.g., in an effective amount. In certain embodiments, the liposome composition can have a PE:PC ratio in a range of from about 50:50 to about 95:5. The composition can, in some embodiments, further include another purified lipid from *Francisella*, for example *F. tularensis*.

In another aspect, the present disclosure provides a liposome comprising purified lipid from *Francisella*, for example a virulent strain of *Francisella tularensis* such as *Francisella tularensis* ssp. *tularensis*. In another embodiment, the disclosure provides a liposome comprising at least one of a purified lipid from *Francisella*, for example a virulent strain of *Francisella tularensis* such as *Francisella tularensis* ssp. *tularensis*, a synthetic phosphatidylethanolamine (PE) or a combination of both. In certain embodiments, the PE and/or the PC comprises an acyl chain with a length in a range of from 5 to 13 carbons. In additional embodiments, the PE and/or the PC comprises an acyl chain of from 20 to 28 carbons. In a particular embodiment, the PE and/or PC has two acyl chains wherein at least one acyl chain has a length of from 20 to 28 carbons. In a particular embodiment, the PE and/or the PC has two acyl chains wherein at least one acyl chain has a length of from 5 to 13 carbons. In certain embodiments, the PE and/or PC has two acyl chains, wherein one chain is from 5 to 13 carbons, and the other chain is in the range of from 20 to 28 carbons.

In a particular embodiment, the liposome is an emulsified liposome. The liposome or the emulsified liposome, according to an embodiment, has a diameter in a range of from about 20 nm to about 1,500 nm.

In an additional aspect, the present disclosure provides an anti-inflammatory liposome composition produced by the following process: adding *Francisella* to a mixture of chloroform/methanol (e.g., 2:1) and mixing; adding water to the organic mixture; separating the organic phase and aqueous phase; drying the organic phase; and reconstituting the dried organic phase, wherein the reconstituted organic phase is the anti-inflammatory composition. In some embodiments, the *Francisella* is a virulent *Francisella tularensis*, such as *Francisella tularensis* ssp. *tularensis*. In a particular embodiment, the chloroform/methanol is at a ratio of about 2:1. In a particular embodiment, the dried organic phase is reconstituted in ethanol.

In other embodiments, the process further comprises adding PC to the isolated lipid of the reconstituted organic phase or the isolated lipid. In certain embodiments, the ratio of the reconstituted organic phase or isolated lipid to PC is in a range of from about 50:50 to about 95:5 (e.g., about 60:40 to about 95:5).

In further embodiments, the process further comprises separating complex *Francisella* lipid via thin layer chromatography (TLC). In an embodiment, a band close to the solvent front was isolated to produce enriched lipid. In some embodiment, the isolated lipid is enriched for PE. In an embodiment, at least one of the PE, the PC, or a combination thereof, comprises at least one acyl chain with a length in a range of from 5 to 13. In certain embodiments, at least one of the PE, the PC, or a combination thereof, comprises at least one acyl chain with a length in a range of from 20 to 28 carbons. In a particular embodiment, the purified lipid is PE, for example, a PE having two acyl chains, wherein at least one acyl chain has a length of from 20 to 28 carbons and/or from 5 to 13 carbons. In a particular embodiment, the purified lipid is PE, for example, a PE having two acyl chains, wherein at least one acyl chain has a length of from 5 to 13 carbons. In certain embodiments, the purified lipid is PE having two acyl chains, wherein one chain is from 5 to 13 carbons, and the other chain is in the range of from 20 to 28 carbons.

In yet other embodiments, the process further comprises adding another purified lipid from *Francisella*, for example *Francisella tularensis*.

In another embodiment, the process further comprises producing a liposome from the reconstituted organic phase, isolated lipid, or isolated lipid-PC mixture, which can be, for example, an emulsified liposome. In an embodiment, the liposome has a diameter in a range of from about 20 nm to about 1,500 nm.

In another aspect, the present disclosure provides a pharmaceutical composition comprising a pharmaceutically effective amount of a liposome (or the anti-inflammatory composition) as described herein. In an embodiment, the pharmaceutical composition further comprises a pharmaceutically acceptable carrier or excipient. In certain embodiments, the composition is in the form of at least one of a liquid, a gel or a cream.

In another aspect, the disclosure provides a liposome composition comprising a modified form of PE, e.g., modified PE isolated from *Francisella tularensis*. There are a wide range of lipid modifications known to those skilled in the art, all of which are expressly contemplated herein, including, e.g., mannosylation. In certain embodiments, the PE is conjugated with another agent, e.g., to another biologically active agent, a homing agent, or to a molecular entity for increasing at least one of half-life, stability, bioavailability or a combination thereof. In certain embodiments, the agent is an antibody, or a PEG molecule.

In another aspect, the disclosure provides a therapeutic composition comprising a liposome (or the anti-inflammatory composition) as described herein in combination with another active agent. In certain embodiments, the agent can be conjugated or associated with the lipids themselves. In still additional embodiments, the agents can be encompassed within the continuous phase of the interior of the liposomes.

In yet a further aspect, the present disclosure provides a method of treating or preventing a microbial infection or inflammation resulting from a microbial infection in a subject, e.g., a patient, in the need thereof. The method comprising administering a composition comprising an effective amount of the liposome (or the anti-inflammatory composition) of present disclosure to a subject in need thereof, wherein the composition or liposome is effective in treating or preventing the microbial infection or the inflammation resulting from a microbial infection. In certain embodiments, the composition further comprises a pharmaceutically acceptable excipient or carrier.

In an embodiment, the microbial infection is a bacterial or a viral infection, for example a bacterial infection or a viral infection that causes dermatological inflammation and/or respiratory inflammation. In a particular embodiment, the bacterial infection or viral infection is selected from the group consisting of *Staphylococcus aureus, Streptococcus pyogenes, Clostridium perfringens, Bacillus anthracis, Francisella tularensis*, measles, rubella, varicella zoster, parvovirus, herpes simplex virus 6, herpes simplex virus 7, herpes simplex virus 8, Epstein Barr virus, enterovirus, coxsackie virus, togavirus, bunyavirus, arenavirus, smallpox, cowpox, monkey pox, zika virus, dengue virus, nairovirus, arenavirus, filovirus, west nile virus, molluscum contagiosm, and human papillomavirus.

In some embodiments, the composition or the liposome is administered prior to exposure to the microbial infection, while in other embodiments, the composition or the liposome is administered post exposure to the microbial infection. In still additional embodiments, the composition is administered before and after microbial infection. In certain embodiments, the method further comprises co-administering the composition or the liposome with one or more additional therapeutic agents.

In a further aspect, the present disclosure provides for a method of treating or preventing inflammation in a subject, e.g., a patient, in the need thereof. The method comprises administering a composition having an effective amount of the liposome (or the anti-inflammatory composition) of the present disclosure to the subject, wherein the composition is effective in alleviating, ameliorating, treating and/or preventing at least one symptom of inflammation in the subject. In an embodiment, the inflammation is related to at least one of a bacterial infection, a viral infection, an autoimmune disease or disorder, and an allergy.

In an additional aspect, the present disclosure provides a method of modulating an immune response in a subject. The method comprises administering a composition comprising an effective amount of the liposome (or the anti-inflammatory composition) of the present disclosure to a subject in need thereof, e.g., a subject having inflammation, wherein the composition is effective in modulating the immune response in the subject. In some embodiments, the modulation comprises enhancing the immunocompetence in the subject, e.g. by suppressing an inflammatory response. In an embodiment, the suppressing an inflammatory response does not affect the patients ability to produce an adaptive immune response.

In a further embodiment, the modulation of an immune response comprises inhibiting bacterial replication in the subject. In other embodiments, the modulation of an immune response comprises inhibiting viral replication in the subject. In some embodiments, the bacterial infection or viral infection is a respiratory infection and/or a dermatological infection.

In certain embodiments, the inflammation is caused by at least one of an autoimmune disease, an autoimmune disorder, an allergy, or a combination thereof. In other embodiments, the subject has dermatological or respiratory inflammation.

The present disclosure provides compositions or liposomes featuring purified lipid from *Francisella* and methods of using such compositions/liposomes for the treatment or prevention of an infectious disease and/or inflammation. Other features and advantages of the invention will be apparent from the detailed description, and from the claims.

BRIEF DESCRIPTION OF THE DRAWINGS

The following detailed description, given by way of example, but not intended to limit the invention solely to the specific embodiments described, may best be understood in conjunction with the accompanying drawings.

Figure 1:
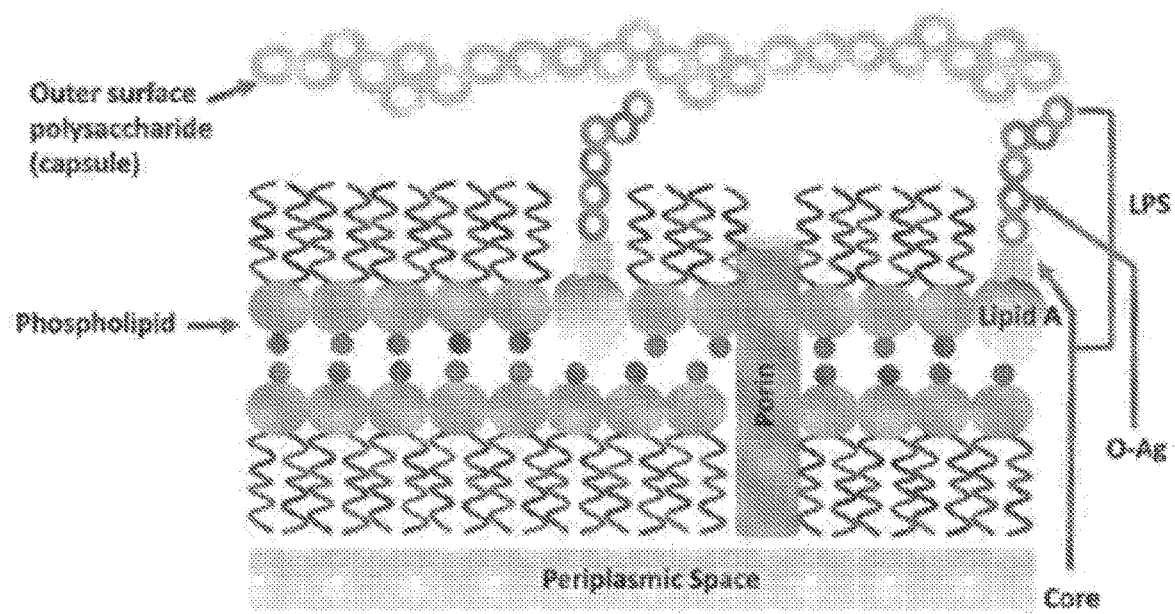
FIG. 1 provides a schematic diagram of a typical Gram-negative outer membrane.

As used herein in the specification and in the claims. "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims. "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase. "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

The term "compound" is to be understood to include any composition or liposome of the present disclosure.

The term "patient" or "subject" is used throughout the specification to describe an animal, including human, non-human primates (e.g., ape or monkey), or a wild/domesticated animals, to whom treatment, including prophylactic treatment, with the compositions according to the present disclosure is provided. For treatment of those infections, conditions or disease states which are specific for a specific animal, such as a human patient, the term patient refers to that specific animal, including a wild or domesticated animal, such as a dog, a cat, a mouse, a hamster, or a farm animal such as a horse, cow, sheep, donkey, pig, chicken, etc.

As used herein, the term "treatment" or "treating" includes any process, action, application, therapy, or the like, wherein a subject (or patient), including a human being, is provided with or administered an agent or composition, e.g., a composition including at least one *Francisella* lipid, with the aim of improving the subject's condition, directly or indirectly, or slowing the progression of a condition or disorder in the subject (e.g., fever or shortness of breath due to infection or an inflammation related disease or disorder), or ameliorating at least one symptom of the disease or disorder under treatment (e.g., cough or diarrhea caused by an infection or disease or disorder related to an inflammatory response—i.e., inflammation). As used in the context of disease caused by a bacteria or viral pathogen, the terms "treat," "treatment," and the like, refer to relief from or alleviation of a pathological process mediated by an inflammatory response or directly affecting the pathogen, for example inhibiting replication.

The terms "co-administration" and "co-administering" or "combination therapy" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain preferred aspects, the composition described herein is coadministered in combination with at least one additional bioactive agent, especially including at least one of an antiviral, antibacterial, anti-mycotic, anti-inflammatory, or another agent that ameliorates signs and/or symptoms of the infection or inflammation related disease or disorder. In particularly preferred aspects, the co-administration of compounds results in synergistic activity and/or therapy. One therapy can be based on the composition of the disclosure. A second (or third, fourth, fifth, sixth, etc.) therapy can be based on a known therapy for the disease/disorder or infection being treated. For example, alternative antiviral or antibacterial drugs may be co-administered with the composition of the disclosure or therapeutic agents to ameliorate symptoms or conditions caused by the infection or disease/disorder being treated or prevented. The order of administration of two or more sequentially co-administered therapeutic agents is not limited. The administration of the two or more therapeutic agents may also be administered by different routes, e.g., by a local route (e.g., mucosal delivery of a dual vaccine of the disclosure) and a systemic route (e.g., parenteral delivery of an anti-rabies or anti-coronavirus small molecule inhibitor).

The term "effective" is used to describe an amount of a compound, composition or component which, when used within the context of its intended use, effects an intended result. The term effective subsumes all other effective amount or effective concentration terms, which are otherwise described or used in the present application.

As used herein, the phrases "therapeutically effective amount" and "prophylactically effective amount" refer to an amount that provides a therapeutic benefit in the treatment, prevention, or management of pathological processes mediated by an infection with a pathogen, or an overt symptom of a pathological processes mediated by an inflammatory response. The specific amount that is therapeutically effective can be readily determined by ordinary medical practitioner, and may vary depending on factors known in the art, such as, e.g. the type of pathological processes mediated by a viral/bacterial infection or the disease/disorder, the patient's history and age, the stage of pathological processes mediated by the infection, disease and/or disorder, and the administration of other anti-pathological agents.

As used herein, a "pharmaceutical composition" comprises a pharmacologically effective amount of a therapeutic agent of the disclosure (such as the anti-inflammatory composition or liposome of the present disclosure) and a pharmaceutically acceptable carrier. As used herein, "pharmacologically effective amount," "therapeutically effective amount" or simply "effective amount" refers to that amount of a composition effective to produce the intended pharmacological, therapeutic or preventive result. For example, if a given clinical treatment is considered effective when there is at least a 25% reduction in a measurable parameter associated with a disease or disorder, a therapeutically effective amount of a drug for the treatment of that disease or disorder is the amount necessary to effect at least a 25% reduction in that parameter. Further, the pharmaceutical composition can be designed to enhance targeting cells involved in the underlying infection such as dendritic cells, macrophages, hepatocytes, and other parenchymal cells, and/or inhibit an inflammatory response associated with an infection, disease and/or disorder. As used herein, the term "pharmaceutically acceptable" means that the subject item is appropriate for use in a pharmaceutical product.

As used herein, the term "isolated" or "purified" lipid or biologically-active portion of lipids thereof is substantially free of other cellular material from the cells that the lipid is obtained.

As used herein, "pharmaceutically acceptable carrier" includes any material which, when combined with an active ingredient of a composition, allows the ingredient to retain biological activity and without causing disruptive reactions with the subject's immune system. Examples include, but are not limited to, any of the standard pharmaceutical carriers such as a phosphate buffered saline solution, water, emulsions such as oil/water emulsion, and various types of wetting agents. Exemplary diluents for aerosol or parenteral administration are phosphate buffered saline or normal (0.9%) saline. Compositions comprising such carriers are formulated by well-known conventional methods (see, for example. Remington's Pharmaceutical Sciences, Chapter 43, 14th Ed., Mack Publishing Col, Easton Pa. 18042, USA). Pharmaceutically acceptable excipients have been amply described in a variety of publications, including, for example, A. Gennaro (2000) "Remington: The Science and Practice of Pharmacy," 20th edition, Lippincott, Williams, & Wilkins; Remington's Pharmaceutical Sciences, 14th Ed. or latest edition, Mack Publishing Col, Easton Pa. 18042, USA; Pharmaceutical Dosage Forms and Drug Delivery Systems (1999) H. C. Ansel et al., eds., 7th ed., Lippincott, Williams, & Wilkins; and Handbook of Pharmaceutical Excipients (2000) A. H. Kibbe et al., eds., 3rd ed. Amer. Pharmaceutical Assoc. Further discussion is provided herein.

As used herein, "ameliorate" is meant decrease, suppress, attenuate, diminish, arrest, or stabilize the development or progression of a disease.

As used herein, "antigen" is meant an agent that induces a humoral and/or cellular immune response.

As used herein, "disease" is meant any condition or disorder that damages or interferes with the normal function of a cell, tissue, or organ. Examples of diseases include bacterial invasion or colonization of a host cell.

As used herein, "liposome" is meant a microscopic vesicle comprising an aqueous core enclosed in one or more phospholipid layers.

As used herein, "pathogen" is meant any bacteria, viruses, fungi, or protozoans capable of interfering with the normal function of a cell. Exemplary bacterial pathogens include, but are not limited to, Aerobacter, *Aeromonas, Acinetobacter Agrobacterium, Bacillus, Bacteroides, Bartonella, Bordetella, Brucella, Burkholderia, Calymmatobacterium, Campylobacter, Citrobacter, Clostridium, Corynebacterium, Enterobacter Escherichia, Francisella, Haemophilus, Hafnia, Helicobacter, Klebsiella, Legionella, Listeria, Morganella, Moraxella, Proteus, Providencia, Pseudomonas, Salmonella, Serratia, Shigella, Staphylococcus, Streptococcus, Treponema, Xanthomonas, Vibrio*, and *Yersinia*.

By "protective immune response" is meant an immune response sufficient to ameliorate a pathogen infection in a mammal.

By "reference" is meant a standard or control condition.

In an aspect, the present disclosure provides an anti-inflammatory composition comprising an effective amount of purified lipid from *Francisella*. The lipid can be purified from a virulent strain from *Francisella tularensis*, which has been shown to induce an anti-inflammatory response. The virulent strain can be *Francisella tularensis* ssp. *tularensis*. In a particular embodiment, the purified lipid has anti-inflammatory properties. In certain embodiments, the purified lipid inhibits inflammation. In an additional embodiment, the purified lipid modulates an immune response. i.e. inhibits inflammation, but does not disrupt the immune system's ability to produce an adaptive immune response. In a particular embodiment, the purified lipid enhances the immune system's ability to produce an adaptive immune response, as compared to a patient that does not receive the purified lipid. In a further embodiment, the purified lipid is a synthetic PE.

In another embodiment, the purified lipid comprises a phosphatidylethanolamine (PE). It was surprising and unexpected to discover that the PE of the purified lipid of *Francisella* has an acyl chain with a length in a range of from 5 to 13 carbons (e.g., C5:0-C13:0). It was also surprising and unexpected to discover that the PE of the purified lipid of *Francisella* has an acyl chain with a length in a range of from 20 to 28 carbons, as PE typically has acyl chains with a length in a range of from 16 to 18 carbons (i.e., C16:0-C18:0). In an embodiment, the purified lipid is enriched for PE. In a particular embodiment, the purified lipid is PE, for example, a PE having two acyl chains, wherein at least one acyl chain has a length of from 20 to 28 carbons. In another embodiment, the purified lipid is PE, for example a PE having two acyl chains wherein at least one acyl chain has a length of from 5 to 13 carbons. In an additional embodiments, the purified lipid is PE, for example a PE having two acyl chains, wherein at least one acyl chain has a length of from 5 to 15 carbons and at least one acyl chain has a length of from 20 to 28 carbons. In certain embodiments, the purified lipid is PE having two acyl chains, wherein one chain is from 5 to 13 carbons (e.g., C5:0-C13:0), and the other chain is in the range of from 20 to 28 carbons (e.g., C20:0-C28:0). In other embodiments, the length of the acyl chain is 5 (e.g., C5:0), 6 (e.g., C6:0), 7 (e.g., C7:0), 8 (e.g. C8:0), 9 (e.g., C9:0), 10 (e.g., C10:0), 11 (e.g., C11:0), 12 (e.g., C12:0), 13 (e.g., C13:0), 20 (e.g., C20:0), 21 (e.g., C21:0), 22 (e.g., C22:0), 23 (e.g., C23:0), 24 (e.g., C24:0), 25 (e.g., C25:0), 26 (e.g., C26:0), 27 (e.g., C27:0), or 28 (e.g., C28:0) carbons. In yet other embodiments, the purified lipid is PE having two acyl chains, wherein one acyl chain is 5 (e.g., C5:0), 6 (e.g., C6:0), 7 (e.g., C7:0), 8 (e.g., C8:0), 9 (e.g., C9:0), 10 (e.g., C10:0), 11 (e.g., C11:0), 12 (e.g., C12:0), or 13 (e.g., C13:0) carbons, and the other acyl chain is 20 (e.g., C20:0), 21 (e.g., C21:0), 22 (e.g., C22:0), 23 (e.g., C23:0), 24 (e.g., C24:0), 25 (e.g., C25:0), 26 (e.g., C26:0), 27 (e.g., C27:0), or 28 (e.g., C28:0) carbons. In a particular embodiment, the PE has the following structure:

It was surprising and unexpected to discover that the PC with an acyl chain with a length in a range of from 20 to 28 carbons had inhibitory activity. In a particular embodiment, the PC has two acyl chains, wherein at least one acyl chain has a length of from 20 to 28 carbons. In an additional embodiment, the PC has two acyl chains, wherein each of the acyl chains has a length of from 20 to 28 carbons. In other embodiments, the length of the acyl chain is 20 (e.g.,

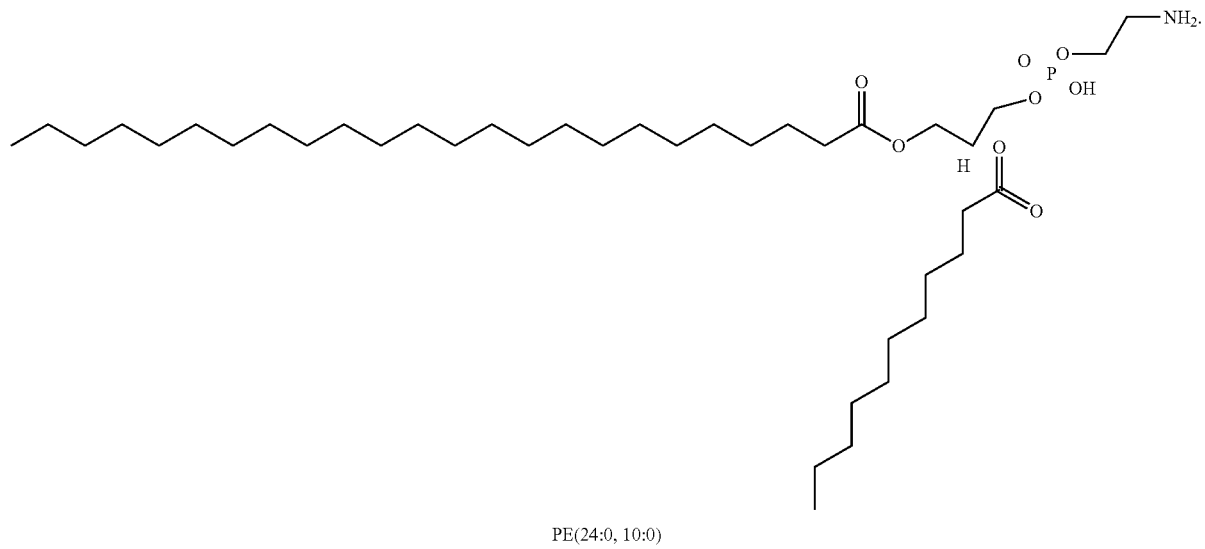

PE(24:0, 10:0)

In certain embodiments, the composition further comprises phosphatidylcholine (PC). In a particular embodiment, the ratio of PE:PC is in a range of from about 50:50 to about 95:5. In an additional embodiment, the ratio of PE:PC is in a range of from: about 55:45 to about 95.5, about 60:40 to about 95:5, about 65:35 to about 95:5, about 70:30 to about 95:5, about 75:25 to about 95:5, about 80:20 to about 95.5, about 85:15 to about 95.5, about 90:10 to about 95:5, about 50:50 to about 90:10, about 55:45 to about 90:10, about 60:40 to about 90:10, about 65:35 to about 90:10, about 70:30 to about 90:10, about 75:25 to about 90:10, about 80:20 to about 90:10, about 85:15 to about 90:10, about 50:50 to about 85:15, about 55:45 to about 85:15, about 60:40 to about 85:15, about 65:35 to about 85:15, about 70:30 to about 85:15, about 75:25 to about 85:15, about 80:20 to about 85:15, about 50:50 to about 80:20, about 55:45 to about 80:20, about 60:40 to about 80:20, about 65:35 to about 80:20, about 70:30 to about 80:20, about 75:25 to about 80:20, about 50:50 to about 75:25, about 55:45 to about 75:25, about 60:40 to about 75:25, about 65:35 to about 75:25, about 70:30 to about 75:25, about 50:50 to about 70:30, about 55:45 to about 70:30, about 60:40 to about 70:30, about 65:35 to about 70:30, about 50:50 to about 65:35, about 55:45 to about 65:35, about 60:40 to about 65:35, about 50:50 to about 60:40, or about 55:45 to about 60:40. In certain embodiments, the ratio of PE:PC is about 50:50, about 55:45, about 60:40, about 61:39, about 62:38, about 63:37, about 64:36, about 65:35, about 66:34, about 67:33, about 68:32, about 69:32, about 70:30; about 71:29, about 72:28, about 73:27, about 74:26, about 75:25, about 76:24, about 77:23, about 78:22, about 79:21, about 80:20, about 81:19, about 82:18, about 83:17, about 84:16, about 85:15, about 86:14, about 87:13, about 88:12, about 89:11, about 90:10, about 91:9, about 92:8, about 93:7, about 94:6, or about 95:5.

C20:0), 21 (e.g., C21:0), 22 (e.g., C22:0), 23 (e.g., C23:0), 24 (e.g., C24:0), 25 (e.g., C25:0), 26 (e.g., C26:0), 27 (e.g., C27:0), or 28 (e.g., C28:0) carbons. In yet other embodiments, the PC has two acyl chains, wherein one acyl chain is 20 (e.g., C20:0), 21 (e.g., C21:0), 22 (e.g., C22:0), 23 (e.g., C23:0), 24 (e.g., C24:0), 25 (e.g., C25:0), 26 (e.g., C26:0), 27 (e.g., C27:0), or 28 (e.g., C28:0) carbons, and the other acyl chain is 20 (e.g., C20:0), 21 (e.g., C21:0), 22 (e.g., C22:0), 23 (e.g., C23:0), 24 (e.g., C24:0), 25 (e.g., C25:0), 26 (e.g., C26:0), 27 (e.g., C27:0), or 28 (e.g., C28:0) carbons.

In a particular embodiment, the PC has two acyl chains, wherein at least one acyl chain has a length of from 5 to 13 carbons. In an additional embodiment, the PC having two acyl chains, wherein at least one acyl chain has a length of from 5 to 15 carbons and at least one acyl chain has a length of from 20 to 28 carbons. In certain embodiments, the PC having two acyl chains, wherein one chain is from 5 to 13 carbons (e.g., C5:0. C6:0, C7:0, C8:0, C9:0, C10:0, C11:0, C12:0, or C13:0), and the other chain is in the range of from 20 to 28 carbons (e.g., C20:0-C28:0), as discussed above.

In some embodiments, the composition further comprises about 5% to about 20% cholesterol. In other embodiments, the PEPC composition comprises about 5% to about 20% cholesterol. Cholesterol further stabilizes the liposomes. In another embodiment, the composition/PEPC composition/liposome of the present disclosure comprises about 5% to about 20%, about 5% to about 15%, about 5% to about 10%, about 10% to about 20%, about 10% to about 15%, or about 15% to about 20% cholesterol.

In another embodiment, the composition further comprises at least one additional purified lipid (e.g., a second, a third, a fourth, a fifth, a sixth, a seventh, an eighth, and/or a ninth lipid) from *Francisella*. The at least one additional purified lipid can be from *F. tularensis*, for example a virulent strain of *F. tularensis*. The virulent strain of *F. tularensis* can be ssp. *tularensis*. In a particular embodiment, the at least one additional purified lipid has anti-inflammatory properties. In certain embodiments, the at least one additional purified lipid inhibits inflammation. In an additional embodiment, the at least one additional purified lipid modulates an immune response, i.e. inhibits inflammation, but does not disrupt the immune system's ability to produce an adaptive immune response. In a particular embodiment, the at least one additional purified lipid enhances the immune system's ability to produce an adaptive immune response, as compared to a patient that does not receive the at least one additional purified lipid.

In other embodiments, the composition is a liposome, e.g. an emulsified liposome. The liposome can have a diameter in a range of from about 20 nm to about 1,500 nm. In certain embodiments, the diameter of the liposome is in a range of: from about 20 nm to about 1,500 nm; from about 100 nm to about 1,500 nm; from about 200 nm to about 1,500 nm; from about 300 nm to about 1,500 nm; from about 400 nm to about 1,500 nm; from about 500 nm to about 1,500 nm; from about 600 nm to about 1,500 nm; from about 700 nm to about 1,500 nm; from about 800 nm to about 1,500 nm; from about 900 nm to about 1,500 nm; from about 1,000 nm to about 1,500 nm; from about 1,100 nm to about 1,500 nm; from about 1,200 nm to about 1,500 nm; from about 1,300 nm to about 1,500 nm; from about 1,400 nm to about 1,500 nm; from about 20 nm to about 1,400 nm; from about 100 nm to about 1,400 nm; from about 200 nm to about 1,400 nm; from about 300 nm to about 1,400 nm; from about 400 nm to about 1,400 nm; from about 500 nm to about 1,400 nm; from about 600 nm to about 1,400 nm; from about 700 nm to about 1,400 nm; from about 800 nm to about 1,400 nm; from about 900 nm to about 1,400 nm; from about 1,000 nm to about 1,400 nm; from about 1,100 nm to about 1,400 nm; from about 1,200 nm to about 1,400 nm; from about 1,300 nm to about 1,400 nm; from about 20 nm to about 1,300 nm; from about 100 nm to about 1,300 nm; from about 200 nm to about 1,300 nm; from about 300 nm to about 1,300 nm; from about 400 nm to about 1,300 nm; from about 500 nm to about 1,300 nm; from about 600 nm to about 1,300 nm; from about 700 nm to about 1,300 nm; from about 800 nm to about 1,300 nm; from about 900 nm to about 1,300 nm; from about 1,000 nm to about 1,300 nm; from about 1,100 nm to about 1,300 nm; from about 1,200 nm to about 1,300 nm; from about 20 nm to about 1,200 nm; from about 100 nm to about 1,200 nm; from about 200 nm to about 1,200 nm; from about 300 nm to about 1,200 nm; from about 400 nm to about 1,200 nm; from about 500 nm to about 1,200 nm; from about 600 nm to about 1,200 nm; from about 700 nm to about 1,200 nm; from about 800 nm to about 1,200 nm; from about 900 nm to about 1,200 nm; from about 1,000 nm to about 1,200 nm; from about 1,100 nm to about 1,200 nm; from about 20 nm to about 1,100 nm; from about 100 nm to about 1,100 nm; from about 200 nm to about 1,100 nm; from about 300 nm to about 1,100 nm; from about 400 nm to about 1,100 nm; from about 500 nm to about 1,100 nm; from about 600 nm to about 1,100 nm; from about 700 nm to about 1,100 nm; from about 800 nm to about 1,100 nm; from about 900 nm to about 1,100 nm; from about 1,000 nm to about 1,100 nm; from about 20 nm to about 1,000 nm; from about 100 nm to about 1,000 nm; from about 200 nm to about 1,000 nm; from about 300 nm to about 1,000 nm; from about 400 nm to about 1,000 nm; from about 500 nm to about 1,000 nm; from about 600 nm to about 1,000 nm; from about 700 nm to about 1,000 nm; from about 800 nm to about 1,000 nm; from about 900 nm to about 1,000 nm; from about 20 nm to about 900 nm; from about 100 nm to about 900 nm; from about 200 nm to about 900 nm; from about 300 nm to about 900 nm; from about 400 nm to about 900 nm; from about 500 nm to about 900 nm; from about 600 nm to about 900 nm; from about 700 nm to about 900 nm; from about 800 nm to about 900 nm; from about 20 nm to about 800 nm; from about 100 nm to about 800 nm; from about 200 nm to about 800 nm; from about 300 nm to about 800 nm; from about 400 nm to about 800 nm; from about 500 nm to about 800 nm; from about 600 nm to about 800 nm; from about 700 nm to about 800 nm; from about 20 nm to about 700 nm; from about 100 nm to about 700 nm; from about 200 nm to about 700 nm; from about 300 nm to about 700 nm; from about 400 nm to about 700 nm; from about 500 nm to about 700 nm; from about 600 nm to about 700 nm; from about 20 nm to about 600 nm; from about 100 nm to about 600 nm; from about 200 nm to about 600 nm; from about 300 nm to about 600 nm; from about 400 nm to about 600 nm; from about 500 nm to about 600 nm; from about 20 nm to about 500 nm; from about 100 nm to about 500 nm; from about 200 nm to about 500 nm; from about 300 nm to about 500 nm; from about 400 nm to about 500 nm; from about 20 nm to about 400 nm; from about 100 nm to about 400 nm; from about 200 nm to about 400 nm; from about 300 nm to about 400 nm; from about 20 nm to about 300 nm; from about 100 nm to about 300 nm; from about 200 nm to about 300 nm; from about 20 nm to about 200 nm; from about 100 nm to about 200 nm; or from about 100 nm to about 200 nm.

In another aspect, the present disclosure provides a liposome comprising purified lipid from *Francisella*, for example a virulent strain of *Francisella tularensis* such as *Francisella tularensis* ssp. *tularensis*. In another embodiment, the purified lipid comprises a phosphatidylethanolamine (PE) as described above.

In further embodiments, the composition further comprises phosphatidylcholine (PC) as described above. The composition can, in some embodiments, further include another purified lipid from *Francisella* as described above.

In a particular embodiment, the liposome is an emulsified liposome. The liposome or the emulsified liposome, according to an embodiment, has a diameter in a range of from about 20 nm to about 1,500 nm.

In an additional aspect, the present disclosure provides an anti-inflammatory composition produced by the following process: adding *Francisella* to a mixture of chloroform/methanol (e.g., 2:1) and mixing, adding water to the organic mixture; separating the organic phase and aqueous phase; drying the organic phase; and reconstituting the dried organic phase, wherein the reconstituted organic phase is the anti-inflammatory composition. In some embodiments, the *Francisella* is a virulent *Francisella tularensis*, such as *Francisella tularensis* ssp. *tularensis*.

In another aspect, the present disclosure provides a method of making an anti-inflammatory composition. The method comprises: adding *Francisella* to a mixture of chloroform/methanol (e.g., 2:1) and mixing; adding water to the organic mixture; separating the organic phase and aqueous phase; drying the organic phase; and reconstituting the dried organic phase, wherein the reconstituted organic phase is the anti-inflammatory composition. In some embodiments, the *Francisella* is a virulent *Francisella tularensis*, such as *Francisella tularensis* ssp. *tularensis*.

In a particular embodiment, the chloroform/methanol is at a ratio in a range of from about 3:1 to about 1:1, such as about 2:1. For example the chloroform/methanol ratio can be about 3:1 to about 1:1, about 2.75:1 to about 1:1, about 2:5 to about 1:1, about 2.25:1 to about 1:1, about 2:1 to about 1:1, about 1.75:1 to about 1:1, about 1.5:1 to about 1:1, about 1.25:1 to about 1:1, about 3:1 to about 1.25:1, about 2.75:1 to about 1.25:1, about 2:5 to about 1.25:1, about 2.25:1 to about 1.25:1, about 2:1 to about 1.25:1, about 1.75:1 to about 1.25:1, about 1.5:1 to about 1.25:1, about 3:1 to about 1.5:1, about 2.75:1 to about 1.5:1, about 2:5 to about 1.5:1, about 2.25:1 to about 1.5:1, about 2:1 to about 1.5:1, about 1.75:1 to about 1.5:1, about 3:1 to about 1.75:1, about 2.75:1 to about 1.75:1, about 2:5 to about 1.75:1, about 2.25:1 to about 1.75:1, about 2:1 to about 1.75:1, about 3:1 to about 2:1, about 2.75:1 to about 2:1, about 2:5 to about 2:1, about 2.25:1 to about 2:1, about 3:1 to about 2.25:1, about 2.75:1 to about 2.25:1, about 2:5 to about 2.25:1, about 3:1 to about 2.5:1, about 2.75:1 to about 2.5:1, or about 3:1 to about 2:0.75. In certain embodiments, the ratio is about 2.75:1, about 2.5:1, about 2.25:1, about 2:1, about 1.75:1, about 1.5:1, about 1.25:1, or about 1:1.

In some embodiment, mixing of *Francisella* and chloroform/methanol is performed, e.g. vigorously, for about 5 minutes to about 25 minutes. In certain embodiments, the mixing of *Francisella* and chloroform/methanol is performed for about 5 to about 25 minutes, about 5 to about 22.5 minutes, about 5 to about 20 minutes, about 5 to about 17.5 minutes, about 5 to about 15 minutes, about 5 to about 12.5 minutes, about 5 to about 10 minutes, about 5 to about 7.5 minutes, about 7.5 to about 25 minutes, about 7.5 to about 22.5 minutes, about 7.5 to about 20 minutes, about 7.5 to about 17.5 minutes, about 7.5 to about 15 minutes, about 7.5 to about 12.5 minutes, about 7.5 to about 10 minutes, about 10 to about 25 minutes, about 10 to about 22.5 minutes, about 10 to about 20 minutes, about 10 to about 17.5 minutes, about 10 to about 15 minutes, about 10 to about 12.5 minutes, about 12.5 to about 25 minutes, about 12.5 to about 22.5 minutes, about 12.5 to about 20 minutes, about 12.5 to about 17.5 minutes, about 12.5 to about 15 minutes, about 15 to about 25 minutes, about 15 to about 22.5 minutes, about 15 to about 20 minutes, about 15 to about 17.5 minutes, about 17.5 to about 25 minutes, about 17.5 to about 22.5 minutes, about 17.5 to about 20 minutes, about 20 to about 25 minutes, about 20 to about 22.5 minutes, or about 22.5 to about 25 minutes. In other embodiments, mixing of *Francisella* and chloroform/methanol is performed for about 5, about 6, about 7, about 8, about 9, about 10, about 11, about 12, about 13, about 14, about 15, about 16, about 17, about 18, about 19, about 20, about 21, about 22, about 23, about 24, or about 25 minutes. In an embodiment, mixing is performed for about 15 minutes.

In an embodiment, the adding of water to the organic mixture includes mixing the mixture. In further embodiments, the mixing of the aqueous and organic mixture is performed, e.g. mixed vigorously, for about 5 to about 15 minutes. In other embodiments, the mixing of the aqueous and organic mixture is performed (i.e., mixed) for about 5 to about 15 minutes, about 5 to about 12.5 minutes, about 5 to about 10 minutes, about 5 to about 7.5 minutes, about 7.5 to about 15 minutes, about 7.5 to about 12.5 minutes, about 7.5 to about 10 minutes, about 10 to about 15 minutes, about 10 to about 12.5 minutes, or about 12.5 to about 15 minutes. In particular embodiments, the mixing of the aqueous and organic mixture is performed for about 5, about 5.5, about 6, about 6.5, about 7, about 7.5, about 8, about 8.5, about 9, about 9.5, about 10, about 10.5, about 11, about 11.5, about 12, about 12.5, about 13, about 13.5, about 14, about 14.5, or about 15 minutes.

In other embodiments, separating the organic phase and the aqueous phase includes centrifuging the mixture at about 3,500×g to about 4,500×g for about 5 to about 15 minutes. For example, the mixture may be centrifuged at about 3500×g to about 4500×g, about 3500×g to about 4250×g, about 3500×g to about 4000×g, about 3500×g to about 3750×g, about 3750×g to about 4500×g, about 3750×g to about 4250×g, about 3750×g to about 4000×g, about 4000×g to about 4500×g, about 4000×g to about 4250×g, or about 4250×g to about 4500×g. In certain embodiments, the mixture is centrifuged at about 3500×g, about 3600×g, about 3700×g, about 3800×g, about 3900×g, about 4000×g, about 4100×g, about 4200×g, about 4300×g, about 4400×g, or about 4500×g. In some embodiments, the mixture is centrifuged for about 5 to about 15 minutes, about 5 to about 12.5 minutes, about 5 to about 10 minutes, about 5 to about 7.5 minutes, about 7.5 to about 15 minutes, about 7.5 to about 12.5 minutes, about 7.5 to about 10 minutes, about 10 to about 15 minutes, about 10 to about 12.5 minutes, or about 12.5 to about 15 minutes. In certain embodiments, the mixture is centrifuged for about 5, about 6, about 7, about 8, about 9, about 10, about 11, about 12, about 13, about 14, or about 15 minutes.

In yet other embodiments, separating the aqueous phase and organic phase comprises removing the organic phase and placing the organic phase into another container. In further embodiments, drying the organic phase is performed under nitrogen. In an embodiment, the dried organic phase is reconstituted in an alcohol (e.g. methanol, ethanol, butanol, and/or pentanol) or chloroform. In some embodiments, the alcohol is at least 90% alcohol, at least about 91% alcohol, at least about 92% alcohol, at least about 93% alcohol, at least about 94% alcohol, at least about 95% alcohol, at least about 96% alcohol, at least about 97% alcohol, at least about 98%, or at least about 99% alcohol. In other embodiments, the alcohol is about 90% alcohol, about 90.5% alcohol, about 91% alcohol, about 91.5% alcohol, about 92% alcohol, about 92.5% alcohol, about 93% alcohol, about 93.5% alcohol, about 94% alcohol, about 94.5% alcohol, about 95% alcohol, about 95.5% alcohol, about 96% alcohol, about 96.5% alcohol, about 97% alcohol, about 97.5% alcohol, about 98% alcohol, about 98.5% alcohol, about 99% alcohol or about 100% alcohol.

In further embodiments, the process further comprises isolating a band of the reconstituted organic phase that runs near the solvent front of thin layer chromatography to produce an isolated lipid. In some embodiment, crude lipid is fractioned to enrich phospholipids and then further fractionated using column chromatography to enrich for PE. As such, the isolated lipid is enriched for PE. In an embodiment, the PE is as described in detail above.

In other embodiments, the process further comprises adding PC to the isolated lipid of the reconstituted organic phase, the isolated lipid, or synthetic PE of the present disclosure. The ratio of the reconstituted organic phase or isolated lipid to PC is as described above in detail.

In yet other embodiments, the process further comprises adding at least one additional purified lipid from *Francisella*, for example *Francisella tularensis*.

In another embodiment, the process further comprises producing a liposome from the reconstituted organic phase, isolated lipid, or isolated lipid-PC mixture, which can be, for example, an emulsified liposome. As described above, PE and PC can be combined in varying ratios from about 50:50 to about 95:5 to obtain liposomes. In some embodiments, the method further comprises adding cholesterol in an amount such that cholesterol comprises about 5 to about 20% of the composition. In other embodiments, the method further comprises adding cholesterol in an amount such that cholesterol comprises about 5 to about 20% of the PEPC liposome. Cholesterol further stabilizes the liposomes. In an embodiment, the liposome has a diameter as described herein, such as a diameter in a range of from about 20 nm to about 1,500 nm.

In another aspect, the present disclosure provides a pharmaceutical composition comprising a pharmaceutically effective amount of the composition (e.g. the anti-inflammatory composition) or the liposome of the present disclosure. In an embodiment, the pharmaceutical composition further comprises a pharmaceutically acceptable carrier, for example a gel or a cream.

Certain embodiments of the disclosure provide pharmaceutical compositions containing one or more other additional therapeutic agents, for example, anti-viral small molecule drug inhibits some aspect of a bacterial or viral infection and/or inflammation related disease/disorder, or which helps to mitigate one or more symptoms of a bacterial or viral infection and/or an inflammation related disease/disorder.

In another aspect, the disclosure provides a therapeutic composition comprising the anti-inflammatory composition or a liposome as described herein in combination with another therapeutic or biologically active agent. In certain embodiments, the agent can be conjugated or associated with the lipids themselves. In still additional embodiments, the agents can be encompassed within the continuous phase of the interior of the liposomes.

The one or more additional therapeutic or biologically active agent can be any standard therapy known in the art. For example, the compositions of the disclosure may, if desired, be administered in combination with an agent that reduces the survival of a pathogen, including but not limited to Aztreonam; Chlorhexidine Gluconate; Imidurea; Lycetamine; Nibroxane; Pirazmonam Sodium; Propionic Acid; Pyrithione Sodium; Sanguinarium Chloride; Tigemonam Dicholine; Acedapsone; Acetosulfone Sodium; Alamecin; Alexidine; Amdinocillin; Amdinocillin Pivoxil; Amicycline; Amlfloxacin; Amifloxacin Mesylate; Amikacin; Amikacin Sulfate; Aminosalicylic acid; Amninosalicylate sodium; Amoxicillin; Amphomycin Ampicillin; Ampicillin Sodium; Apalcillin Sodium; Apramycin; Aspartocin; Astromicin Sulfate; Avilamycin; Avoparcm; Azithromycin; Azlocillin; Azlocillin Sodium; Bacampicillin Hydrochloride; Bacitracin; Bacitracin Methylene Disalicylate; Bacitracin Zinc; Bambermycins; Benzoylpas Calcium; Berythromycin; Betamicin Sulfate; Biapenem; Biniramycin; Biphenamine Hydrochloride; Bispyrithione Magsulfex; Butikacin; Butirosin Sulfate; Capreomycin Sulfate; Carbadox; Carbenicillin Disodium; Carbenicillin Indanyl Sodium; Carbenicillin Phenyl Sodium; Carbenicillin Potassium; Carumonam Sodium; Cefaclor; Cefadroxil; Cefamandole; Cefamandole Nafate; Cefamandole Sodium; Cefaparole; Cefatrizine; Cefazaflur Sodium; Cefazolin; Cefazolin Sodium; Celbuperazone; Cefdinir; Cefepime; Cefepime Hydrochloride; Cefetecol; Cefixime; Cefinenoxime Hydrochloride; Cefmetazole; Cefmetazole Sodium; Cefonicid Monosodium; Cefonicid Sodium; Cefoperazone Sodium; Ceforanide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceflazidime; Ceftibuten; Ceftiioxime Sodium; Cefiriaxone Sodium; Cefuroxime; Cefuroxime Axetil; Cefuroxime Pivoxetil; Cefuroxime Sodium; Cephacetrile Sodium; Cephalexin; Cephalexin Hydrochloride; Cephaloglycin; Cephaloridine; Cephalothin Sodium; Cephapirin Sodium; Cephradine; Cetocycline Hydrochloride; Cetophenicol; Chloramphenicol; Chloramphenicol Palmitate; Chloramphenicol Pantothenate Complex; Chloramphenicol Sodium Succinate; Chlorhexidine Phosphanilale; Chloroxylenol; Chlortetracycline Bisulfate; Chlortetracycline Hydrochloride; Cinoxacin; Ciprofloxacin; Ciprofloxacin Hydrochloride; Cirolemycin; Clarithromycin; Clinafloxacin Hydrochloride; Clindamycin; Clindamycin Hydrochloride; Clindamycin Palmitate Hydrochloride; Clindamycin Phosphate; Clofazimine; Cloxacillin Benzathine; Cloxacillin Sodium; Cloxyquin; Colistimethate Sodium; Colistin Sulfate; Coumermycin; Coumermycin Sodium; Cyclacillin; Cycloserine; Dalfopristin; Dapsone; Daptomycin; Demeclocycline; Demeclocycline Hydrochloride; Demecycline; Denofungin; Diaveridine; Dicloxacillin; Dicloxacillin Sodium; Dihydrostreptomycin Sulfate; Dipyrithione; Dirithromycin; Doxycycline; Doxycycline Calcium; Doxycycline Fosfatex; Doxycycline Hyclate; Droxacm Sodium; Enoxacin; Epicillin; Epitetracycline Hydrochloride; Erythromycin; Erythromycin Acistrate; Erythromycin Estolate; Erythromycin Ethylsuccinate; Erythromycin Gluceptate; Erythromycin Lactobionate; Erythromycin Propionate; Erythromycin Stearate; Ethambutol Hydrochloride; Ethionamide; Fleroxacin; Floxacillin; Fludalanine; Flumequine; Fosfomycin; Fosfomycin Tromethamine; Fumoxicillin; Furazolium Chloride; Furazolium Tartrate; Fusidate Sodium; Fusidic Acid; Gentamicin Sulfate; Gloximonam; Gramicidin; Haloprogin; Hetacillin; Hetacillin Potassium; Hexedine; Ibafloxacin; Imipenem; Isoconazole; Isepamicin; Isoniazid; Josamycin; Kanamycin Sulfate; Kitasamycin; Levofuraltadone; Levopropylcillin Potassium; Lexithromycin; Lincomycin; Lincomycin Hydrochloride; Lomefloxacin; Lomefloxacin Hydrochloride; Lomefloxacin Mesylate; Loracarbef; Mafenide; Meclocycline; Meclocycline Sulfosalicylate; Megalomicin Potassium Phosphate; Mequidox; Meropenem; Methacycline; Methacycline Hydrochloride; Methenamine; Methenamine Hippurate; Methenamine Mandelate; Methicillin Sodium; Metioprim; Metronidazole Hydrochloride; Metronidazole Phosphate; Mezlocillin; Mezlocillin Sodium; Minocycline; Minocycline Hydrochloride; Mirincamycin Hydrochloride; Monensin; Monensin Sodium; Nafcillin Sodium; Nalidixate Sodium; Nalidixic Acid; Natamycin; Nebramycin; Neomycin Palmitate; Neomycin Sulfate; Neomycin Undecylenate; Netilmicin Sulfate; Neutramycin; Nifuradene; Nifuraldezone; Nifuratel; Nifuratrone; Nifurdazil; Nifurimide; Nifurpinnol; Nifurquinazol; Nifurthiazole; Nitrocycline; Nitrofurantoin; Nitromide; Norfloxacin; Novobiocin Sodium; Ofloxacin; Ormetoprim; Oxacillin Sodium; Oximonam; Oximonam Sodium; Oxolinic Acid; Oxytetracycline; Oxytetracycline Calcium; Oxytetracycline Hydrochloride; Paldinmycin; Parachlorophenol; Paulomycin; Pefloxacin; Pefloxacin Mesylate; Penamecillin; Penicillin G Benzathine; Penicillin G Potassium; Penicillin G Procaine; Penicillin G Sodium; Penicillin V; Penicillin V Benzathine; Penicillin V Hydrabamine; Penicillin V Potassium; Pentizidone Sodium; Phenyl Aminosalicylate; Piperacillin Sodium; Pirbenicillin Sodium; Pindicillm Sodium; Pirlimycin Hydrochloride; Pivampicillin Hydrochloride; Pivampicillin Pamoate Pivampicillin Probenate; Polymyxin B Sulfate; Porfiromycin; Propikacin; Pyrazinamide; Pyrithione Zinc; Quindecamine Acetate; Quinupristin; Racephenicol; Ramoplanin; Ranimycin; Relomycin; Repromicin; Rifabutin; Rifametane; Rifamexil; Rifamide; Rifampin; Rifapentine; Rifaximin; Rolitetracycline; Rolitetracycline Nitrate; Rosaramicin; Rosaramicin Butyrate; Rosaramicin Propionate; Rosaramicin Sodium Phosphate; Rosaramicin Stearate; Rosoxacil; Roxarsone; Roxithromycin; Sancycline; Sanfetrinem Sodium; Sarmoxicillin; Sarpicillin; Scopafungin; Sisomicin; Sisomicin Sulfate; Sparfloxacin; Spectinomycin Hydrochloride; Spiramycin; Stallimycin Hydrochloride; Steffimycin; Streptomycin Sulfate; Streptonicozid; Sulfabenz; Sulfabenzamide; Sulfacetamide; Sulfacetamide Sodium; Sulfacytine; SulTfdiazine; Sulfadiazine Sodium; Sulfadoxine; Sulfalene Sulfamerazine; Sulfameter; Sulfamethazine; Sulfamethizole; Sulfamethoxazole; Sulfamonomethoxine; Sulfamoxole; Sulfanilate Zinc; Sulfanitran; Sulfasalazine; Sulfasomizole; Sulfathiazole; Sulfazamet; Sulfisoxazole; Sulfisoxazole Acetyl; Sulfisoxazole Diolamine; Sulfomyxin; Sulopenem; Sultamicillin; Suncillin Sodium; Talampicillin Hydrochloride; Teicoplanin; Temafloxacin Hydrochloride; Temocillin; Tetracycline; Tetracycline Hydrochloridc; Tetracycline Phosphate Complex; Tetroxoprim; Thiamphenicol; Thiphencillin Potassium; Ticarcillin Cresyl Sodium; Ticarcillin Disodium; Ticarcillin Monosodium; Ticlatone; Tiodonium Chloride; Tobramycin; Tobramycin Sulfate; Tosufloxacin; Trimethoprim; Trimethoprim Sulfate; Trisulfapyrimidines; Troleandomycin; Trospectomycin Sulfate; Tyrothricin; Vancomycin; Vancomycin Hydrochloride; Virginiamycin; Zorbamycin; Difloxacin Hydrochloride; Lauryl Isoquinolinium Bromide; Moxalactam Disodium; Omidazole; Pentisomicin; and Sarafloxacin Hydrochloride. See, generally, The Merck Manual of Diagnosis and Therapy, 15th Ed. 1987, pp. 1206-1228, Berkow et al., eds., Rahway, N.J. When used with the composition of the disclosure, such therapeutic agents may be used individually, sequentially, or in combination with one or more other such therapeutic agents. Anti-inflammatory drugs, including but not limited to nonsteroidal anti-inflammatory drugs (e.g., naproxen dodium, celecoxib, sulindac, oxaprozin, salsalate, diflunisal, piroxicam, indomethacin, etodolac, meloxicam, naproxen, nabumetone, ketorolac tromethamine, naproxen/esomeprazole, diclofenac, ibuprofine, and/or aspirin) and corticosteroids (e.g., bethamethasone, prednisone, prednisolone, triamcinolone, methylprednisolone, dexamethasone, hydrocortisone, cortisone, ethamethasoneb, and/or fludrocortisone), and antiviral drugs (including but not limited to amantadine, rimantadine, oseltamivir, zanamivi, acyclovir, brivudine, docosanol, famiciclovir, idoxuridine, penciclovir, valacyclovir, ribavirin, gangciclovir, trifluoridine, zidovudine, didanosine, zalcitabine, lamivudine, abacavir, atazanavir, atripla, idovudine, combivir, darunavir, didanosine, delavirdine, dolutegravir, efavirenz, elvitegravir, enfuvirtide, etravirine, eviplera, fosamprenavir, emtricitabine, indinavir, kivexa, lopinavir, ritonavir, maraviroc, nelfinavir, nevirapine, raltegravir, rilpivirine, ritonavir, saquinavir, stribild, tenofovir, tenofovir, tipranavir, triomine, trizivir, truvada, and α-interfereon) may also be combined in compositions of the disclosure. See, generally, The Merck Manual of Diagnosis and Therapy, 15th Ed., Berkow et al., eds., 1987, Rahway, N.J., pages 2499-2506 and 46-49, respectively). Other therapeutic agents are also within the scope of this disclosure. Two or more combined compounds may be used together or sequentially. Such compounds may be administered using a separate administration schedule relative to the administration schedule of the active agents of the disclosure. The administration schedules may also be the same or have overlap.

In yet a further aspect, the present disclosure provides a method of treating or preventing a microbial infection or inflammation resulting from a microbial infection in a patient in the need thereof. The method comprises administering a composition comprising an effective amount of the liposome (or the anti-inflammatory composition) of present disclosure, wherein the composition or liposome is effective in treating or preventing the microbial infection or the inflammation resulting from a microbial infection.

In an embodiment, the microbial infection is a bacterial or a viral infection, for example a bacterial infection or a viral infection that causes inflammation, e.g. inflammation of the epidermis and/or respiratory system.

In particular embodiments, the invention provides for the treatment of bacterial infections, including infections with gram negative and gram positive bacteria. Such gram positive bacteria include, but are not limited to, *Pasteurella* species, *Staphylococci* species, and *Streptococcus* species. Gram negative bacteria include, but are not limited to, *Escherichia coli*, *Pseudomonas species*, and *Salmonella* species. Specific examples of infectious bacteria include but are not limited to, *Helicobacter* pyloris, *Burkholderia* sps, *Borellia burgdorferi*, *Legionella pneumophilia*, Mycobacteria sps (e.g. *M. tuberculosis, M. avium, M. intracellulare, M. kansasii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus anthracis, Corynebacterium diphtheriae, Corynebacterium* sp., *Erysipelothrix rhusiopathiae, Clostridium perfringens, Clostridium tetani, Enterobacter aerogenes, Klebsiella pneumoniae, Pasteurella multocida, Bacteroides* sp., *Fusobacterium nucleatum*, Sluptobacillus maniliformis, *Treponema pallidium, Treponema pertenue, Leptospira, Rickettsia* ssp, *Yersinia pestis* and *Actinomyces israeli*.

In still other embodiments, the methods of the invention can be used to treat or prevent a viral infection. Exemplary viral pathogens include but are not limited to: Retroviridae (e.g. human immunodeficiency viruses, such as HIV-1 (also referred to as HDTV-III, LAVE or HTLV-II/LAV, or HIV-III; and other isolates, such as HIV-LP; Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronoviridae (e.g. coronaviruses); Rhabdoviridae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthormyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxviridae (variola viruses, vaccinia viruses, pox viruses); and Iridoviridae (e.g. African swine fever virus); and unclassified viruses (e.g. the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astroviruses).

In a particular embodiment, the bacterial infection or viral infection is the bacterial infection or viral infection is selected from the group consisting of *Staphylococcus aureus, Streptococcus pyogenes, Clostridium perfringens, Bacillus anthracis, Francisella tularensis, Corynebacterium diphtheria, Streptococcus pneumoniae, Haemophilus influenza, Bordetella pertussis, Mycobacterium tuberculosis* or *bovis, Mycoplasma pneumoniae, Legionella pneumophila, Chlamydia psittaci, Chlamydia pneumoniae, Coxiella burnetii,* measles, rubella, varicella zoster, parvovirus, herpes simplex virus 6, herpes simplex virus 7, herpes simplex virus 8, Epstein Barr virus, enterovirus, coxsackie virus, togavirus, coronavirus, rhinovirus, bunyavirus, arenavirus, smallpox, cowpox, monkey pox, zika virus, dengue virus, nairovirus, arenavirus, filovirus, west nile virus, molluscum contagiosm, human papillomavirus, coronavirus, rhinovirus, respiratory syncytial virus, and Influenzavirus.

In some embodiments, the composition or the liposome is administered prior to exposure to the microbial infection, while in other embodiments, the composition or the liposome is administered post exposure to the microbial infection. In certain embodiments, the composition or the liposome is administered both before and after infection. In certain embodiments, the method further comprises co-administering the composition or the liposome with one or more additional therapeutic agents.

In a further aspect, the present disclosure provides for a method of treating or preventing inflammation in a subject, e.g., a patient, in the need thereof. The method comprises administering a composition comprising an effective amount of the liposome (or the anti-inflammatory composition) of the present disclosure to a subject in need thereof, wherein the composition is effective in treating or preventing inflammation in the subject. In an embodiment, the inflammation is related to at least one of a bacterial infection, a viral infection, an autoimmune disease or disorder, and an allergy.

In an additional aspect, the present disclosure provides a method of modulating an immune response in a subject. The method comprises administering a composition comprising an effective amount of the liposome (or the anti-inflammatory composition) of the present disclosure to a subject in need thereof, e.g., a subject suffering from inflammation, wherein the composition is effective in modulating the immune response of the subject. In some embodiments, the modulation comprises enhancing the immunocompetence in the subject, e.g. by suppressing an inflammatory response. In an embodiment, the suppressing an inflammatory response does not affect the patients ability to produce an adaptive immune response.

In a further embodiment, the modulation of an immune response comprises inhibiting microbial replication, e.g. bacterial replication or viral replication, in the patient. In some embodiments, the bacterial infection or viral infection is a respiratory infection and/or a epidermal infection.

In certain embodiments, the inflammation is caused by at least one of an autoimmune (or autoimmune related) disease or disorder, an inflammatory disease or disorder, an allergy, or a combination thereof. In other embodiments, the subject has dermatological or respiratory inflammation. In certain embodiments, the autoimmune (or autoimmune related) disease or disorder is selected from the group consisting of Acute Disseminated Encephalomyelitis (ADEM), acute necrotizing hemorrhagic leukoencephalitis, Addison's disease, Agammaglobulinemia, Alopecia areata, Amyloidosis, Ankylosing spondylitis. Anti-GBM/Anti-TBM nephritis. Antiphospholipid syndrome (APS), autoimmune angioedema, autoimmune aplastic anemia, autoimmune dysautonomia, autoimmune hepatitis, autoimmune hyperlipidemia, autoimmune immunodeficiency, autoimmune inner ear disease (AIED), autoimmune myocarditis, autoimmune oophoritis, autoimmune pancreatitis, autoimmune retinopathy, autoimmune thrombocytopenic purpura (ATP), autoimmune thyroid disease, autoimmune urticarial, axonal & neuronal neuropathies. Balo disease, Behcet's disease, Bullous pemphigoid, cardiomyopathy, Castleman disease, Celiac disease, Chagas disease, chronic inflammatory demyelinating polyneuropathy (CIDP), chronic recurrent multifocal ostomyelitis (CRMO), Churg-Strauss syndrome, Cicatricial pemphigoid/benign mucosal pemphigoid, Crohn's disease, Cogans syndrome, cold agglutinin disease, congenital heart block, coxsackie myocarditis, CREST disease, essential mixed cryoglobulinemia, demyelinating neuropathies, dermatitis herpetiformis, dermatomyositis, devic's disease (neuromyelitis optica), discoid lupus, Dressler's syndrome, endometriosis, eosinophilic esophagitis, eosinophilic fasciitis, erythema nodosum, experimental allergic encephalomyelitis, Evans syndrome, fibrosing alveolitis, giant cell arteritis (temporal arteritis), giant cell myocarditis, glomerulonephritis, Goodpasture's syndrome, Granulomatosis with Polyangiitis (GPA) (formerly called Wegener's Granulomatosis), Graves' disease, Guillain-Barre syndrome. Hashimoto's encephalitis, Hashimoto's thyroiditis, Hemolytic anemia, Henoch-Schonlein purpura, Herpes gestationis, hypogammaglobulinemia, idiopathic thrombocytopenic purpura (ITP), IgA nephropathy, IgG4-related sclerosing disease, immunoregulatory lipoproteins, inclusion body myositis, interstitial cystitis, juvenile arthritis, juvenile diabetes (Type 1 diabetes), juvenile myositis, Kawasaki syndrome, Lambert-Eaton syndrome, leukocytoclastic vasculitis, Lichen planus, Lichen sclerosus, Ligneous conjunctivitis, Linear IgA disease (LAD), Lupus (SLE), Lyme disease (chronic), Meniere's disease, microscopic polyangiitis, mixed connective tissue disease (MCTD), Mooren's ulcer, Mucha-Habermann disease, multiple sclerosis. Myasthenia gravis, myositis, narcolepsy, neuromyelitis optica (Devic's), neutropenia, ocular cicatricial pemphigoid, optic neuritis, palindromic rheumatism, PANDAS (Pediatric Autoimmune Neuropsychiatric Disorders Associated with *Streptococcus*), paraneoplastic cerebellar degeneration, paroxysmal nocturnal hemoglobinuria (PNH), Parry Romberg syndrome, Parsonnage-Turner syndrome, pars planitis (peripheral uveitis), pemphigus, peripheral neuropathy, perivenous encephalomyelitis, Pernicious anemia, POEMS syndrome, polyarteritis nodosa, type I, II, & III autoimmune polyglandular syndromes, polymyalgia rheumatic, polymyositis, postmyocardial infarction syndrome, postpericardiotomy syndrome, progesterone dermatitis, primary biliary cirrhosis, primary sclerosing cholangitis, psoriasis, psoriatic arthritis, idiopathic pulmonary fibrosis, pyoderma gangrenosum, pure red cell aplasia, Raynauds phenomenon, reactive Arthritis, reflex sympathetic dystrophy, Reiter's syndrome, relapsing polychondritis, restless legs syndrome, retroperitoneal fibrosis, rheumatic fever, rheumatoid arthritis, sarcoidosis, schmidt syndrome, scleritis, scleroderma, Sjogren's syndrome, sperm and/or testicular autoimmunity, stiff person syndrome, subacute bacterial endocarditis (SBE), Susac's syndrome, sympathetic ophthalmia, Takayasu's arteritis, temporal arteritis/giant cell arteritis, thrombocytopenic purpura (TTP), Tolosa-Hunt syndrome, transverse myelitis, type 1 diabetes, ulcerative colitis, undifflerentiated connective tissue disease (UCTD), uveitis, vasculitis, vesiculobullous dermatosis, vitiligo, or Wegener's granulomatosis (now termed Granulomatosis with Polyangiitis (GPA)).

In another embodiment, the inflammatory disease is selected from the group consisting of Alzheimer's, ankylosing spondylitis, arthritis (including osteoarthritis, rheumatoid arthritis (RA), and/or psoriatic arthritis), asthma, atherosclerosis, Barrett's esophagus, chronic Lyme disease, Crohn's disease, colitis, dermatitis, diabetes, diverticulitis, fibromyalgia, gastroesophageal reflux disease, hepatitis, interstitial cystitis, irritable bowel syndrome (IBS), Löfgren's syndrome, systemic lupus erythematous (SLE), multiple sclerosis, nephritis, Parkinson's disease, polymyalgia rheumatica, prostatitis, psoriasis, psoriatic arthritis, Sjögren's syndrome, ulcerative colitis, and uveitis.

In further embodiments, the disease or disorder associated with inflammation is selected from the group consisting of allergies, Alzheimer's, anemia, ankylosing spondylitis, asthma, autism, arthritis, carpal tunnel syndrome, celiac, crohn's disease, eczema, fibromyalgia, fibrosis, gall bladder disease, GERD, Guillain-Barre, hashimoto's thyroiditis, lupus, multiple sclerosis, pancreatitis, psoriasis, polymyalgia rheumatica, rheumatoid arthritis, scleroderma, and stroke.

The present disclosure provides compositions or liposomes featuring purified lipid from *Francisella* and methods of using such compositions/liposomes for the treatment or prevention of an infectious disease and/or inflammation. Other features and advantages of the invention will be apparent from the detailed description, and from the claims.

As used herein, the terms "treat," "treating." "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

The therapeutic methods of the invention (which include prophylactic treatment) in general comprises administration of a therapeutically effective amount of the compositions or liposome of the present disclosure to a subject (e.g., animal, human) in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). The compositions and/or liposomes of the present disclosure may be also used in the treatment of any other disorders in which a pathogen infection may be implicated.

In one embodiment, the invention provides a method of monitoring treatment progress. The method includes the step of determining a level of diagnostic marker (Marker) (e.g., any target delineated herein modulated by the composition described herein, a protein or indicator thereof, etc.) or diagnostic measurement (e.g., screen, assay) in a subject suffering from or susceptible to a disease/disorder or symptoms thereof associated with a pathogen infection or inflammatory disease/disorder, in which the subject has been administered a therapeutic amount of a composition herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

Therapeutic Compositions

In another aspect, the present disclosure provides a pharmaceutical composition comprising a pharmaceutically effective amount of a liposome or the anti-inflammatory composition of the present disclosure. In an embodiment, the pharmaceutical composition further comprises a pharmaceutically acceptable carrier or excipient. In certain embodiments, the composition is in the form of at least one of a liquid, a gel or a cream.

In another aspect, the disclosure provides a liposome composition comprising a modified form of PE, e.g., modified PE isolated from *Francisella tularensis*. There are a wide range of lipid modifications known to those skilled in the art, all of which are expressly contemplated herein, including. e.g., mannosylation. In certain embodiments, the PE is admixed with or conjugated to another agent, e.g., to another biologically active agent, a homing agent, or to a molecular entity, such as a molecular entity for increasing at least one of half-life, stability, bioavailability or a combination thereof. In certain embodiments, the agent is an antibody or a PEG molecule.

Pharmaceutical compositions comprising combinations of an effective amount of the composition (e.g., the anti-inflammatory composition) or liposome of the present disclosure, in combination with a pharmaceutically effective amount of a carrier, additive and/or excipient, represents a further aspect of the present disclosure.

The compounds as described herein may, in accordance with the disclosure, be administered in single or divided doses by the oral, parenteral or topical routes. Administration of the active composition may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal, sublingual and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Administration of composition according to the present disclosure as sprays, mists, or aerosols for intra-nasal, intra-tracheal or pulmonary administration may also be used. The present disclosure therefore also is directed to pharmaceutical compositions comprising an effective amount of the compositions as described herein, optionally in combination with a pharmaceutically acceptable carrier, additive or excipient. Compositions according to the present disclosure may be administered in immediate release, intermediate release or sustained or controlled release forms. Sustained or controlled release forms are preferably administered orally, but also in suppository and transdermal or other topical forms. Intramuscular injections in liposomal form may also be used to control or sustain the release of compound at an injection site.

The compositions as described herein may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions, including pharmaceutical compositions and liposomes, of the present disclosure may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions as described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1, 3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions as described herein may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions, as described herein, may be administered in the form of suppositories for rectal administration. These can be prepared by mixing the agent with a suitable non-irritating excipient, which is solid at room temperature but liquid at rectal temperature and therefore will melt in the rectum to release the drug. Such materials include cocoa butter, beeswax and polyethylene glycols.

The pharmaceutical compositions as described herein may also be administered topically. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For topical applications, the pharmaceutical compositions may be formulated in a suitable ointment containing the active component suspended or dissolved in one or more carriers. Carriers for topical administration of the compounds of this disclosure include, but are not limited to, mineral oil, liquid petrolatum, white petrolatum, propylene glycol, polyoxyethylene, polyoxypropylene compound, emulsifying wax and water. In certain preferred aspects of the disclosure, the compounds may be coated onto a stent which is to be surgically implanted into a patient in order to inhibit or reduce the likelihood of occlusion occurring in the stent in the patient.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyl-dodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions as described herein may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of the composition or liposome of the present disclosure in a pharmaceutical composition as described herein that may be combined with the carrier materials to produce a single dosage form will vary depending upon the host and disease treated, the particular mode of administration. Preferably, the compositions should be formulated to contain between about 0.01 milligram to about 750 milligrams or more, more preferably about 1 milligram to about 600 milligrams, and even more preferably about 10 milligrams to about 500 milligrams of active composition according to the present disclosure.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject in need of therapy using compositions, including liposome(s), according to the methods of the present disclosure can be treated by administering to the patient (subject) an effective amount of the composition (including liposome) according to the present disclosure, optionally in a pharmaceutically acceptable carrier or diluent, either alone, or in combination with additional agents as otherwise described herein.

These compositions can be administered by any appropriate route, for example, orally, parenterally, intravenously, intradermally, subcutaneously, or topically, including transdermally, in liquid, cream, gel, or solid form, or by aerosol form.

The composition is included in the pharmaceutically acceptable carrier or diluent in an amount sufficient to deliver to a patient a therapeutically effective amount for the desired indication, without causing serious toxic effects in the patient treated. A preferred dose of the composition for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from about 0.01 to about 5% wt/wt in a suitable carrier.

The composition is conveniently administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient.

The composition is preferably administered to achieve peak plasma concentrations of the active components of the composition is about 0.00001-30 mM, preferably about 0.1-30 µM. This may be achieved, for example, by the intravenous injection of a solution or formulation of the composition, optionally in saline, or an aqueous medium or administered as a bolus of the active components of the composition. Oral administration is also appropriate to generate effective plasma concentrations of active agent.

The concentration of active components in the drug composition will depend on absorption, distribution, inactivation, and excretion rates of the drug as well as other factors known to those of skill in the an. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active component(s) can be incorporated with excipients and used in the form of tablets, troches, or capsules. Pharmaceutically compatible binding agents can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active components or composition of the disclosure can be administered as a component of an elixir, suspension, syrup, wafer, chewing gum or the like. A syrup may contain, in addition to the active compounds, sucrose as a sweetening agent and certain preservatives, dyes and colorings and flavors.

The active component(s) or composition of the disclosure can also be mixed with other active materials that do not impair the desired action, or with materials that supplement the desired action, such as anti-viral agents, antibacterial agents, anti-inflammatories, among other agents. In certain preferred aspects of the disclosure, the composition according to the present disclosure are coadministered with another bioactive agent, such as an antibiotic, an antiviral, or a known anti-inflammatory, or an agent to ameliorate a symptom or condition associated with the diseases or disorders described herein.

Solutions or suspensions used for parenteral, intradermal, subcutaneous, or topical application can include the following components: a sterile diluent such as water for injection, saline solution, fixed oils, polyethylene glycols, glycerin, propylene glycol or other synthetic solvents; and/or other agents as described herein. The parental preparation can be enclosed in ampoules, disposable syringes or multiple dose vials made of glass or plastic.

If administered intravenously, preferred carriers are physiological saline or phosphate buffered saline (PBS).

In one embodiment, the compositions of the present disclosure are prepared with carriers that will protect the active components against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal may be prepared according to methods known to those skilled in the art, for example, as described in U.S. Pat. No. 4,522,811 (which is incorporated herein by reference in its entirety). For example, liposome formulations may be prepared by dissolving the purified lipid(s), isolated lipids, and lipid compositions as described herein in an inorganic solvent that is then evaporated, leaving behind a thin film of dried lipid on the surface of the container. An aqueous solution of the active compound is then introduced into the container. The container is then swirled by hand to free lipid material from the sides of the container and to disperse lipid aggregates, thereby forming the liposomal suspension.

A pharmacological composition or formulation refers to a composition or formulation in a form suitable for administration, e.g., systemic administration, into a cell or subject, preferably a human. By "systemic administration" is meant in vivo systemic absorption or accumulation of drugs in the blood stream followed by distribution throughout the entire body. Suitable forms, in part, depend upon the use or the route of entry, for example oral, transdermal, or by injection. Such forms should not prevent the composition or formulation from reaching a target cell (i.e., a cell to which the negatively charged polymer is desired to be delivered to). For example, pharmacological compositions injected into the blood stream should be soluble. Other factors are known in the art, and include considerations such as toxicity and forms which prevent the composition or formulation from exerting its effect.

Administration routes which lead to systemic absorption include, without limitations: intravenous, subcutaneous, intraperitoneal, inhalation, oral, intrapulmonary and intramuscular. The rate of entry of a drug into the circulation has been shown to be a function of molecular weight or size. The use of drug carrier comprising the compounds of the present disclosure can potentially localize the drug, for example, in certain tissue types, such as the skin or respiratory system or the epidermis. A liposome formulation can facilitate the association of drug with the surface of cells, such as, lymphocytes and macrophages.

The present disclosure also features the use of the composition comprising surface-modified liposomes containing poly (ethylene glycol) lipids (PEG-modified, or long-circulating liposomes or stealth liposomes). Compositions of the present disclosure can also comprise covalently attached PEG molecules of various molecular weights. These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. Chem. Rev. 1995, 95, 2601-2627; Ishiwata et al., Chem. Pharm. Bull. 1995, 43, 1005-1011).

The present disclosure also includes compositions prepared for storage or administration that include a pharmaceutically effective amount of the desired components in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit 1985) hereby incorporated by reference herein. For example, preservatives, stabilizers, dyes and flavoring agents can be provided. These include sodium benzoate, sorbic acid and esters of p-hydroxybenzoic acid. In addition, antioxidants and suspending agents can be used.

An effective amount, pharmaceutically effective dose, therapeutically effective amount, or pharmaceutically effective amount is that dose required to prevent, inhibit the occurrence, or treat (alleviate a symptom to some extent, preferably all of the symptoms) of a disease state or pathological condition. The effective amount depends on the type of disease, the composition used, the mute of administration, the type of mammal being treated, the physical characteristics of the specific mammal under consideration, concurrent medication, and other factors which those skilled in the medical arts will recognize. Generally, an amount between 0.1 mg/kg and 1000 mg/kg body weight/day of active ingredients is administered. In addition, effective amounts of the compositions of the disclosure encompass those amounts utilized in the examples to facilitate the intended or desired biological effect.

Toxicity and therapeutic efficacy of such compositions or active ingredients can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions/active ingredients that exhibit large therapeutic indices are preferred. While compositions/active ingredients that exhibit toxic side effects may be used, care should be taken to design a delivery system that targets such compositions or ingredients to the site of affected tissue in order to minimize potential damage to uninfected cells and, thereby, reduce side effects. The data obtained from the cell culture assays and animal studies can be used in formulating a range of dosage for use in humans. The dosage of such compositions/active ingredients lies preferably within a range of circulating concentrations that include the ED50 with little or no toxicity. The dosage may vary within this range depending upon the dosage form employed and the route of administration utilized. For any composition used in the method of the present disclosure, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The formulations can be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a peptide of the disclosure and a pharmaceutically acceptable carrier. One or more peptides of the disclosure can be present in association with one or more non-toxic pharmaceutically acceptable carriers and/or diluents and/or adjuvants, and if desired other active ingredients. The pharmaceutical compositions of the present disclosure can be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any method known to the art for the manufacture of pharmaceutical compositions and such compositions can contain one or more such sweetening agents, flavoring agents, coloring agents or preservative agents in order to provide pharmaceutically elegant and palatable preparations. Tablets contain the active ingredient in admixture with non-toxic pharmaceutically acceptable excipients that are suitable for the manufacture of tablets. These excipients can be for example, inert diluents, such as calcium carbonate, sodium carbonate, lactose, calcium phosphate or sodium phosphate, granulating and disintegrating agents, for example, corn starch, or alginic acid; binding agents, for example starch, gelatin or acacia, and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monosterate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example *arachis* oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present. Pharmaceutical compositions of the present disclosure can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol, glucose or sucrose. Such formulations can also contain a demulcent, a preservative and flavoring and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

For administration to non-human animals, the composition can also be added to the animal feed or drinking water. It can be convenient to formulate the animal feed and drinking water compositions so that the animal takes in a therapeutically appropriate quantity of the composition along with its diet. It can also be convenient to present the composition as a premix for addition to the feed or drinking water. The composition can also be administered to a subject in combination with other therapeutic compounds to increase the overall therapeutic effect. The use of multiple compounds to treat an indication can increase the beneficial effects while reducing the presence of side effects.

A further object of the present disclosure is to provide a kit comprising a suitable container, the therapeutic of the present disclosure in a pharmaceutically acceptable form disposed therein, and instructions for its use.

Preparations for administration of the therapeutic of the present disclosure include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Vehicles include sodium chloride solution, Ringer's dextrose, dextrose and sodium chloride, lactated Ringer's intravenous vehicles including fluid and nutrient replenishers, electrolyte replenishers, and the like. Preservatives and other additives may be added such as, for example, antimicrobial agents, anti-oxidants, chelating agents and inert gases and the like.

The composition (which includes "active compounds" or "active ingredients") of the disclosure can be incorporated into pharmaceutical compositions suitable for administration. Such compositions typically comprise the composition of the present disclosure and a pharmaceutically acceptable carrier. As used herein, "pharmaceutically acceptable carrier" is intended to include any and all solvents, dispersion media, coatings, antibacterial agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the present disclosure is formulated to be compatible with its intended route of administration. Examples of routes of administration include parenteral, e.g., intravenous, intradermal, subcutaneous, oral (e.g., inhalation), transdermal (i.e., topical), transmucosal, intraperitoneal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents, antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor™. (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups, or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia), non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated to give controlled release of the active compound. For buccal administration the compositions may take the form of tablets or lozenges formulated in conventional manner. For administration by inhalation, the compounds for use according to the present disclosure are conveniently delivered in the form of an aerosol spray presentation from pressurized packs or a nebuliser, with the use of a suitable propellant, e.g., dichlorodifluoromethane, trichlorofluoromethane, dichlorotetrafluoroethan-e, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions, or emulsions in oily or aqueous vehicles, and may contain formulatory agents such as suspending, stabilizing, and/or dispersing agents. Alternatively, the active ingredient may be in powder form for constitution with a suitable vehicle, e.g., sterile pyrogen-free water, before use. The compounds may also be formulated in rectal compositions such as suppositories or retention enemas, e.g., containing conventional suppository bases such as cocoa butter or other glycerides. In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

In one embodiment, the compositions are prepared with carriers that will protect the active ingredients against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds/compositions can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred.

The data obtained from cell culture assays and animal studies can be used in formulation a range of dosage for use in patients, e.g. humans. The dosage of compositions of the disclosure lies generally within a range of circulating concentrations that include the ED50 with little or no toxicity. The dosage may vary within this range depending upon the dosage form employed and the route of administration utilized. For any compound/composition used in the method of the disclosure, the therapeutically effective dose can be estimated initially from cell culture assays. A dose may be formulated in animal models to achieve a circulating plasma concentration range of the compound/composition or, when appropriate, of the polypeptide product of a target sequence (e.g., achieving a decreased concentration of the polypeptide) that includes the IC50 (i.e., the concentration of the test compound which achieves a half-maximal inhibition of symptoms), as determined in cell culture. Such information can be used to more accurately determine useful doses for a patient, as defined above (includes, e.g., humans, dogs, cats, etc.). Levels in plasma may be measured, for example, by high performance liquid chromatography.

In addition to their administration individually or as a plurality, as discussed above, the compositions of the disclosure can be administered in combination with other known agents effective in treatment of pathological processes mediated by an inflammatory response caused by a bacterial infection, viral infection, or an inflammatory disease or disorder. In any event, the administering physician can adjust the amount and timing of composition administration on the basis of results observed using standard measures of efficacy known in the art or described herein.

Kits

The invention provides kits for the treatment or prevention of a pathogen infections and/or inflammatory related diseases and disorders. In one embodiment, the kit includes a therapeutic or prophylactic composition containing an effective amount of a liposome formulation or an anti-inflammatory composition formulation in unit dosage form. In some embodiments, the kit comprises a sterile container, which contains a therapeutic or prophylactic cellular composition; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

If desired a cell of the invention is provided together with instructions for administering the agent to a subject having or at risk of developing a pathogen infection or infectious disease, such as a bacterial or viral infection, and/or a disease or disorder related to an inflammatory response, e.g., autoimmunity, asthma, arthritis, and/or psoriasis. The instructions will generally include information about the use of the composition for the treatment or prevention of a pathogen infection or inflammation-related disease or disorder. In other embodiments, the instructions include at least one of the following: description of the therapeutic agent; dosage schedule and administration for treatment or prevention of a pathogen infection and/or a disease/disorder related to inflammation, or symptoms thereof; precautions; warnings; indications; counter-indications; adverse reactions; animal pharmacology; clinical studies; and/or references. The instructions may be printed directly on the container (when present), or as a label applied to the container, or as a separate sheet, pamphlet, card, or folder supplied in or with the container.

The practice of the present disclosure employs, unless otherwise indicated, conventional techniques of molecular biology (including recombinant techniques), microbiology, cell biology, biochemistry and immunology, which are well within the purview of the skilled artisan. Such techniques are explained fully in the literature, such as, Sambrook et al., Molecular Cloning: A Laboratory Manual, 2nd Ed., Cold Spring Harbor Laboratory Press, New York (1989); Kaufman et al., Eds., Handbook of Molecular and Cellular Methods in Biology in Medicine. CRC Press, Boca Raton (1995); McPherson, Ed., Directed Mutagenesis: A Practical Approach, IRL Press, Oxford (1991). Standard reference works setting forth the general principles of pharmacology include Goodman and Gilman's The Pharmacological Basis of Therapeutics, 11th Ed., McGraw Hill Companies Inc., New York (2006). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the disclosure, and are not intended to limit the scope of what the inventors regard as their invention.

EXAMPLES

Example 1. SchuS4 Inhibits Pro-Inflammatory Responses Among Resting Primary Human Cells

Example 1A. Secretion of Pro-Inflammatory Cytokines by hDC Following Infection with *F. tularensis*

Figure 2A:
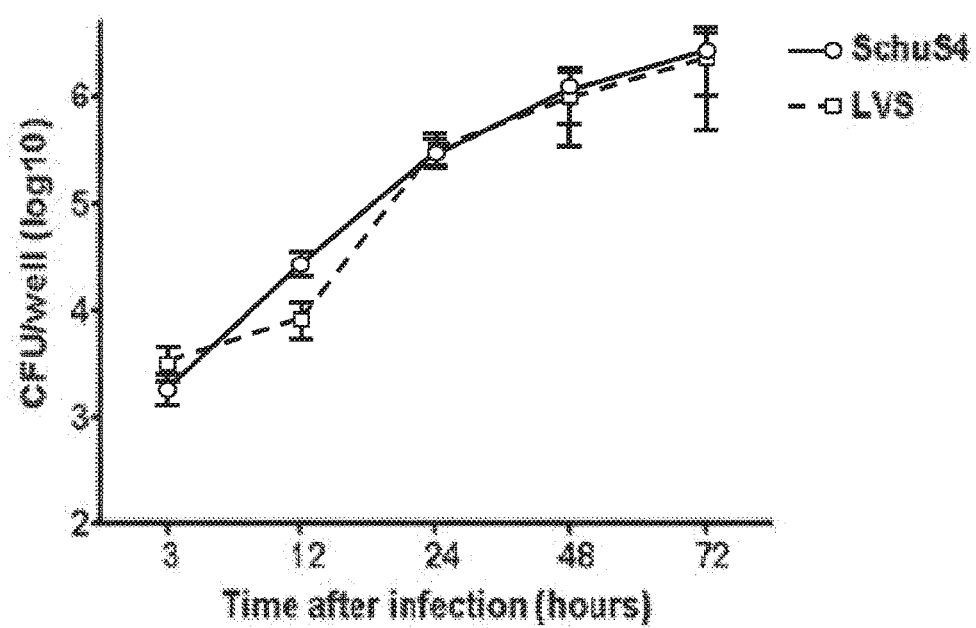
FIGS. 2A, 2B, and 2C demonstrate that SchuS4 inhibits pro-inflammatory responses among resting primary human cells. Differential induction of pro-inflammatory cytokines by attenuated and virulent strains of *F. tularensis*. Primary human dendritic cells (hDC) were infected at a multiplicity of infection of 50 with the indicated strains of *F. tularensis*. (A) Intracellular bacteria were enumerated at the indicated times postinfection. *$p<0.01$, compared with SchuS4-infected hDC. (B) Supernatants were harvested from uninfected or *F. tularensis*-infected cultures at 24 hours postinfection and analyzed for IL-12p40 by ELISA. hDC stimulated 24 h prior to harvest with ultrapure *E. coli* LPS (10 ng/ml) served as positive controls. *$p<0.01$, compared with uninfected and SchuS4-infected hDC; **$p<0.001$, compared with all samples. (C) SchuS4- or mock-infected hDC cultures were stimulated 24 hours postinfection with ultrapure *E. coli* LPS. Concentrations of IL-12p40 in culture supernatants were determined an additional 24 h after LPS treatment. *$p<0.01$, compared with uninfected, LPS-treated samples. Error bars represent SEM. Each data point represents the mean of triplicate samples. Data in (A) are the mean of eight experiments; data in (B) and (C) are representative of three experiments of similar design.
Figure 2B:
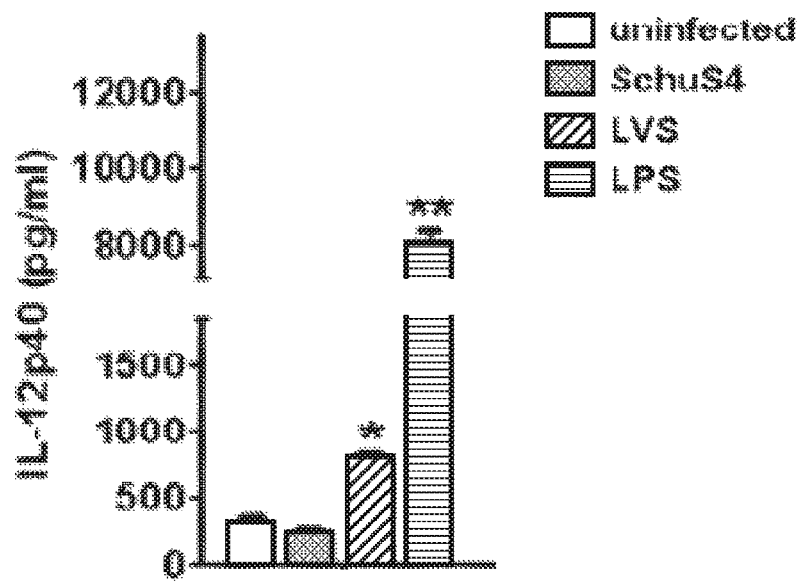

It was suggested that one difference between virulent and attenuated strains of *F. tularensis* is the ability of virulent strains to evade induction of pro-inflammatory responses. Thus, the inventors first compared bacterial replication and secretion of IL-12p40 into culture supernatants following infection of hDC with either virulent *F. tularensis* strain SchuS4 or attenuated *F. tularensis* strain LVS. Similar numbers of SchuS4 and LVS were phagocytosed by hDC (FIG. 2A). However, SchuS4 replicated more quickly over the first 12 hours of infection compared with LVS. Similar numbers of LVS and SchuS4 were recovered from hDC at 24, 48, and 72 hours postinfection (FIG. 2A). In agreement with our and others' previous observations, SchuS4 failed to stimulate secretion of IL-12p40 in concentrations that were significantly different from uninfected hDC, whereas LVS induced significantly more IL-12p40 compared with uninfected and SchuS4-infected cells at each time point tested (FIG. 2B). These data demonstrate that one difference between SchuS4 and LVS is the ability of SchuS4 to undergo intracellular replication without provoking inflammatory cytokines.

Figure 2C:
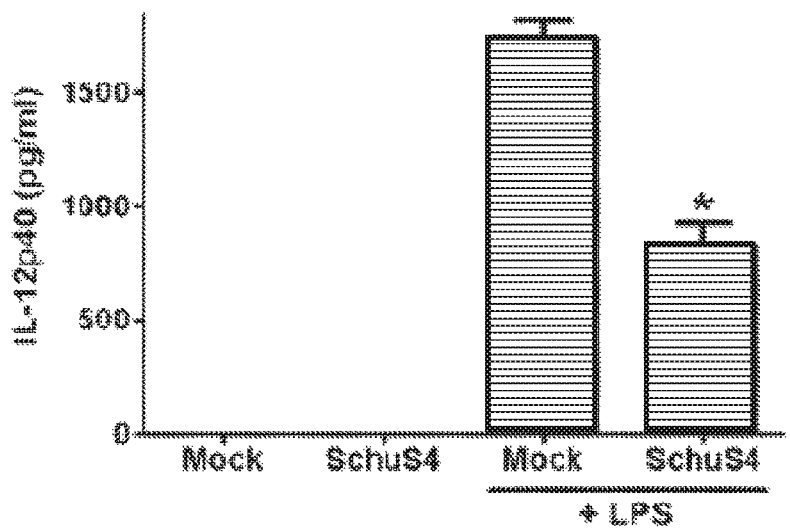

Example 1B. SchuS4 Actively Interferes with Secretion of Pro-Inflammatory Cytokines It was confirmed that SchuS4 was actively inhibiting secretion of pro-inflammatory cytokines in hDC following infection. Twenty-four hours postinfection. *E. coli* LPS was added to hDC cultures, and secretion of IL-12p40 was measured 24 hours later. Consistent with our previous observations using intracellular cytokine staining, hDC infected with SchuS4 produced significantly less IL-12p40 compared with uninfected cells in response to *E. coli* LPS (FIG. 2C). Thus, SchuS4 fails to induce inflammatory responses in hDC and actively inhibits their ability to secrete proinflammatory cytokines in response to secondary microbial stimuli.

Figure 3:
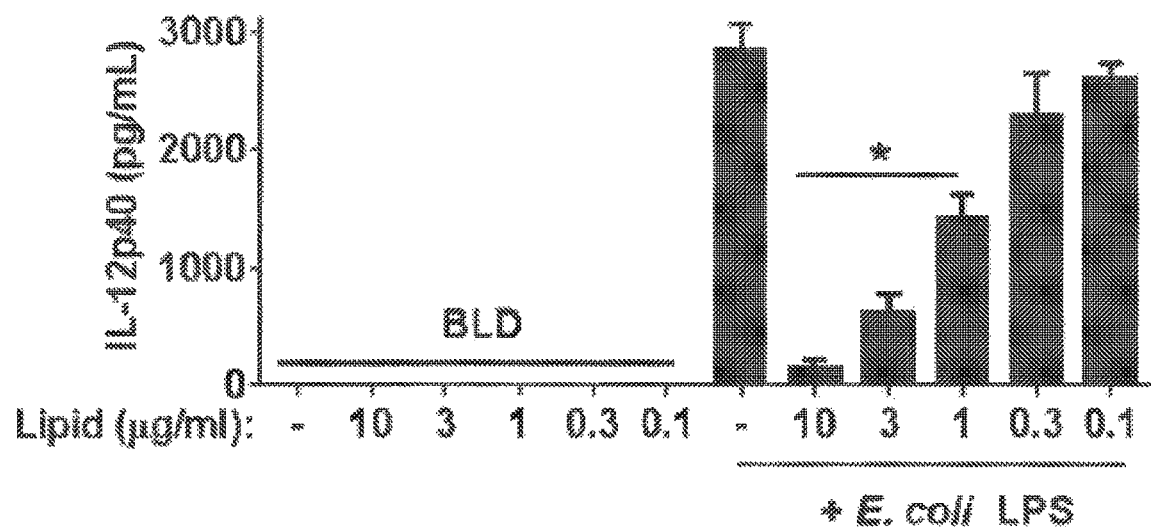
FIG. 3 demonstrates that SchuS4 lipids inhibit inflammatory responses in vitro. hDC were treated with the indicated concentration of lipids isolated from SchuS4 or LVS for 18 hours followed by addition of LPS for an additional 20 hours. EtOH served as vehicle control. Culture supernatants were assessed for IL-12p40 by ELISA. ns=not significantly different. *=significantly less than EtOH+LPS treated controls ($p<0.05$). In each experiment, each condition was tested in triplicate. Error bars represent SEM. Data is representative of three experiments of similar design using different donors.

Example 2. SchuS4 Lipids Inhibit Inflammatory Responses In Vitro hDC were treated with the indicated concentration of lipids isolated from SchuS4 or LVS for 18 hours followed by addition of LPS for an additional 20 hours. EtOH served as vehicle control. Culture supernatants were assessed for IL-12p40 by ELISA (FIG. 3). ns=not significantly different. *=significantly less than EtOH+LPS treated controls ($p<0.05$). In each experiment each condition was tested in triplicate. Error bars represent SEM. Data is representative of three experiments of similar design using different donors.

Example 3. SchuS4 Lipids Inhibit Pulmonary Inflammation In Vivo

Figure 4A:
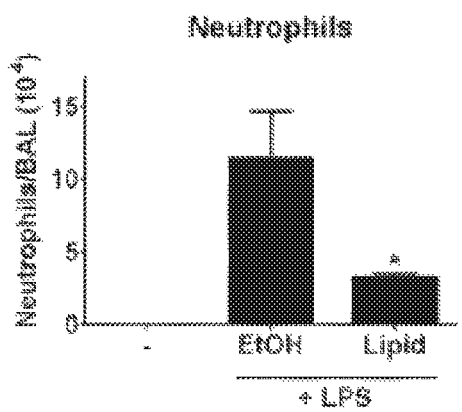
FIGS. 4A and 4B demonstrate that SchuS4 lipids inhibit pulmonary inflammation. Mice (n=5/group) were intranasally inoculated with 25 μg/25 μl SchuS4 lipids or 25 μl diluted EtOH. Eighteen hours later, mice were treated with 200 ng/25 μl *E. coli* LPS. Five hours after administration of LPS, mice were euthanized and fluid and cells from the airways were collected by bronchoalveolar lavage. Completely unmanipulated (−) mice served as negative controls. (A) Infiltration of neutrophils was evaluated by flow cytometry. (B) BAL fluid was assessed for TNF-α, IL-6, and KC by ELISAs. Error bars, SEMs. *, P<0.05, compared to EtOH-treated controls. Data are representative of two experiments of similar design.
Figure 4B:
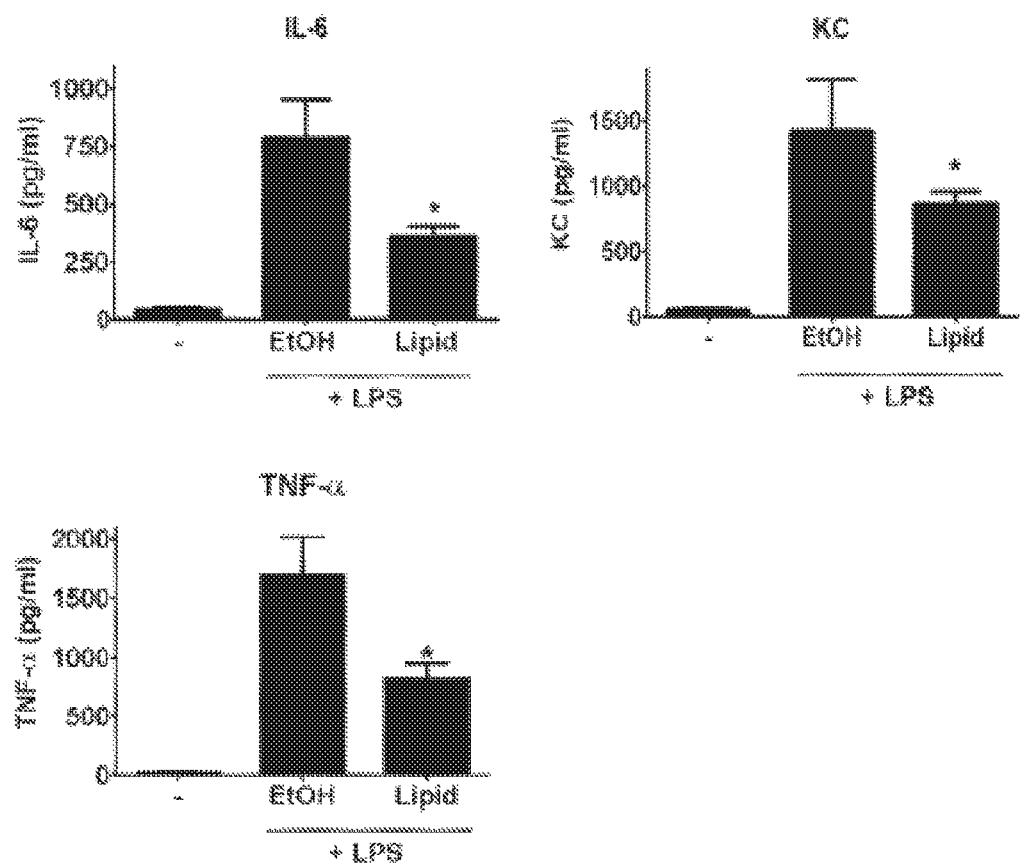

Mice exposed to SchuS4 lipids had significantly fewer neutrophils in their airways in response to LPS than did EtOH-treated controls (FIG. 4A). However, neutrophils that were recruited to the airways of SchuS4 lipid-treated mice expressed levels of CD11b similar to those observed in EtOH-treated controls. The inventors did not observe changes in MHC-II expression on macrophages from any mice treated with LPS at the time point assessed. Exposure to SchuS4 lipids also significantly reduced the amounts of TNF-$\alpha$, IL-6, and KC detected in the airways of mice following exposure to LPS, compared to EtOH-treated controls (FIG. 4B). RANTES levels were not significantly increased above levels in untreated controls for any group (data not shown). Together, these data suggest that, while SchuS4 lipids fail to induce inflammatory responses in the lung, these bacterial components significantly attenuate secondary pulmonary inflammation.

Example 4. Identification of Active SchuS4 Lipid

Figure 5A:
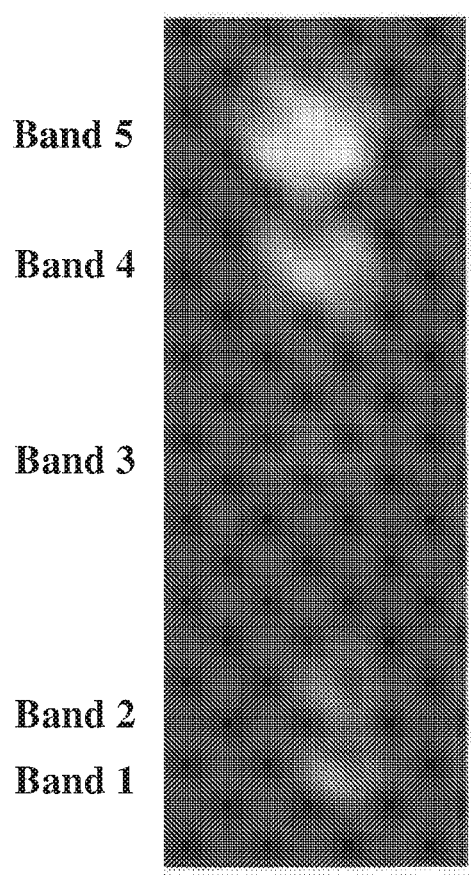
FIGS. 5A, 5B, and 5C identifies an active portion of the SchuS4 lipid preparation. Crude SchuS4 lipids were separated by TLC (A) and the indicated bands were scraped from the silica plate and assessed for their junction with open-ended language such as "comprising" can refer, in one embodiment, to A only (optionally including elements other than B); in another embodiment, to B only (optionally including elements other than A); in yet another embodiment, to both A and B (optionally including other elements); etc.
Figure 5B:
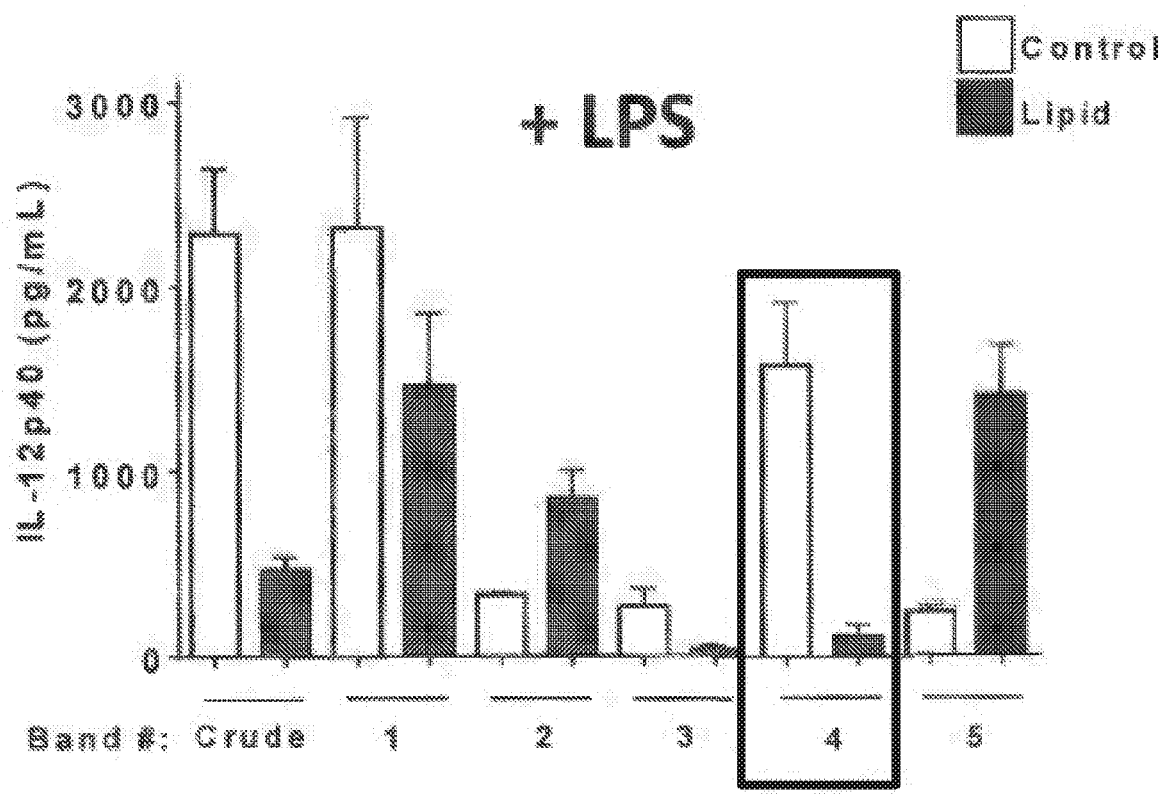
Figure 5C:
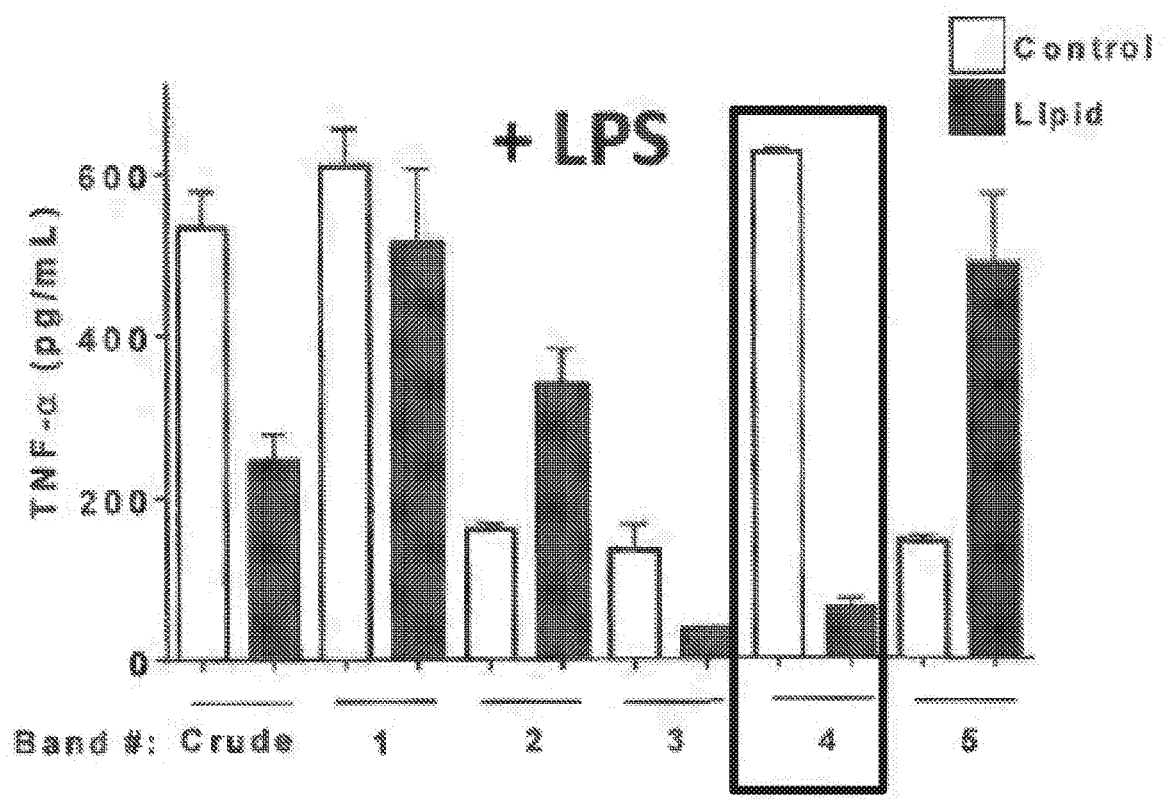

Crude SchuS4 lipids were separated by TLC (FIG. 5A) and the indicated bands were scraped from the silica plate and assessed for their ability to inhibit inflammatory responses in hDC (FIGS. 5B and 5C). Areas of the TLC plate at the same part of the solvent front, but not containing lipid were scraped as used as negative controls. hDC were treated and supernatants were assessed for the indicated cytokines as described in FIG. 3. Following incubation with lipid and LPS supernatants were assessed for IL-12p40 (B) or TNF-$\alpha$ (C) by ELISA. Error bars represent SD. Band 4 from the TLC plate was analyzed by LC-MS for lipid content and speciation.

Figure 6A:
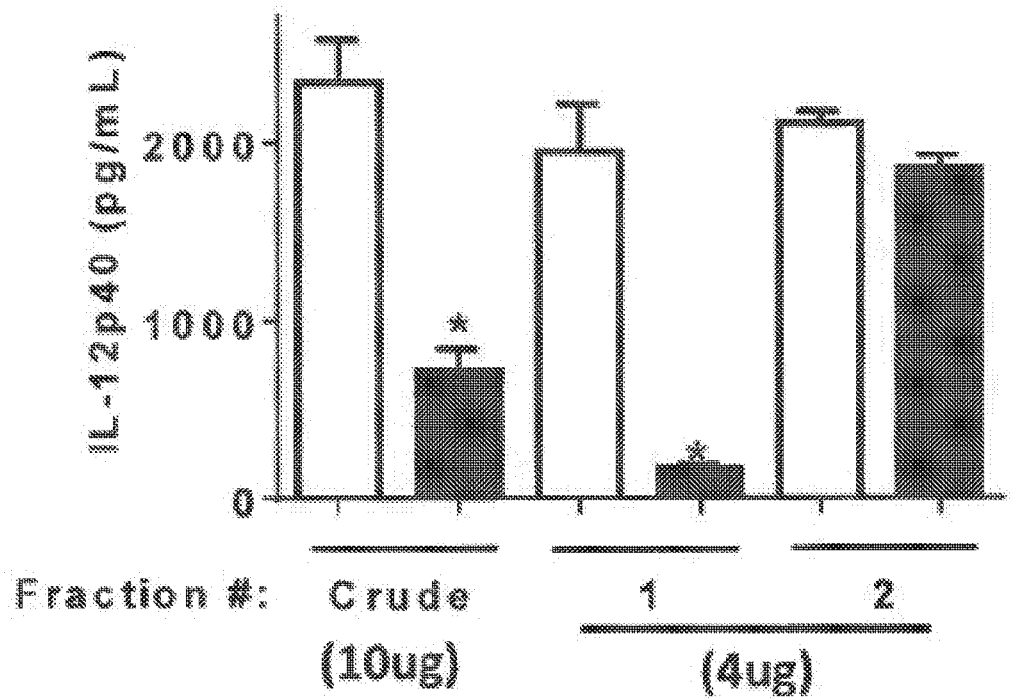
Figure 6B:
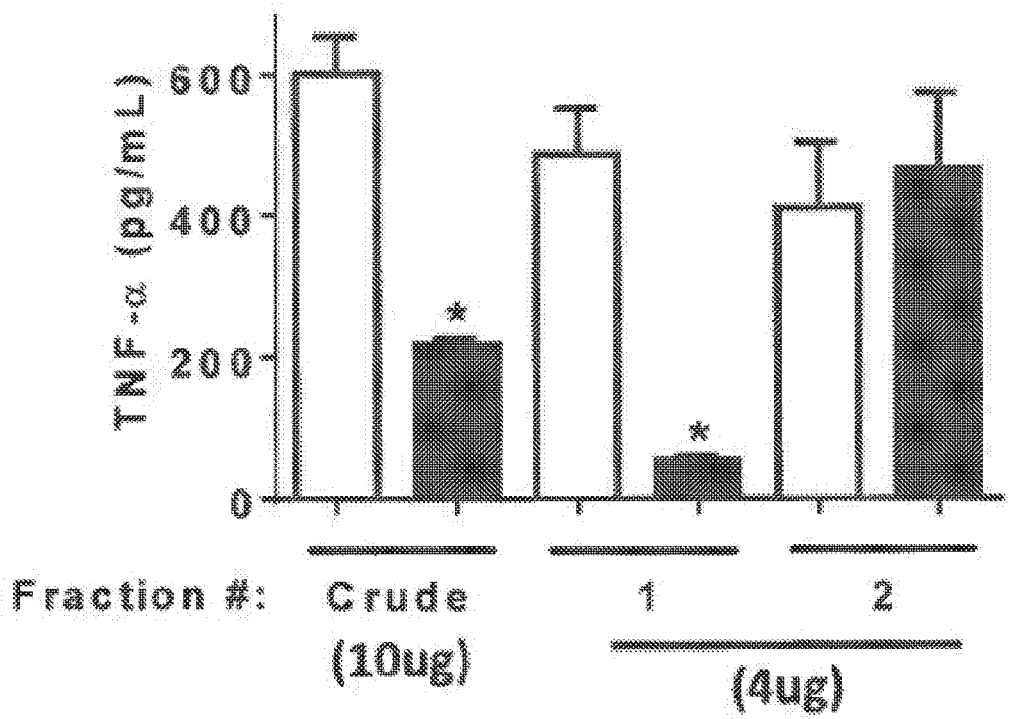

Phospholipids from crude SchuS4 lipid preparations were isolated and fractionated into PE (1) or PC (2) containing fractions. These samples, or crude lipid, were added to hDC at the indicated concentrations. Cells were treated with LPS as described in FIG. 3 (black bars) or treated with media alone (white bars). Supernatants were assessed for IL-12p40 (FIG. 6A) or TNF-$\alpha$ (FIG. 6B) by ELISA. Error bars represent SD. *=$p<0.05$.

Example 5. Generation and Testing of Synthetic 24:10 PE

Figure 7A:
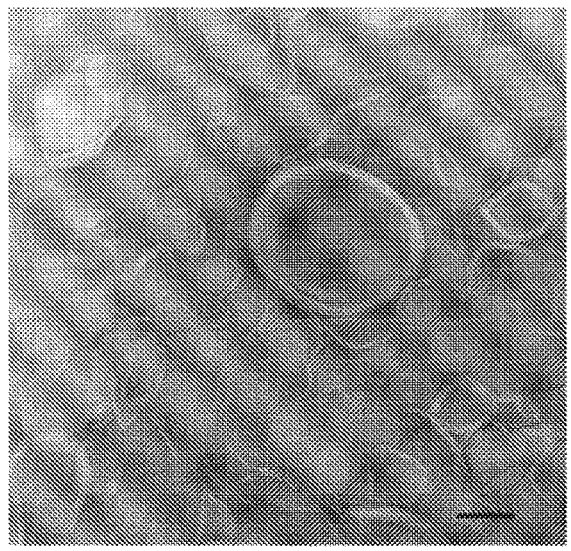
Figure 7B:
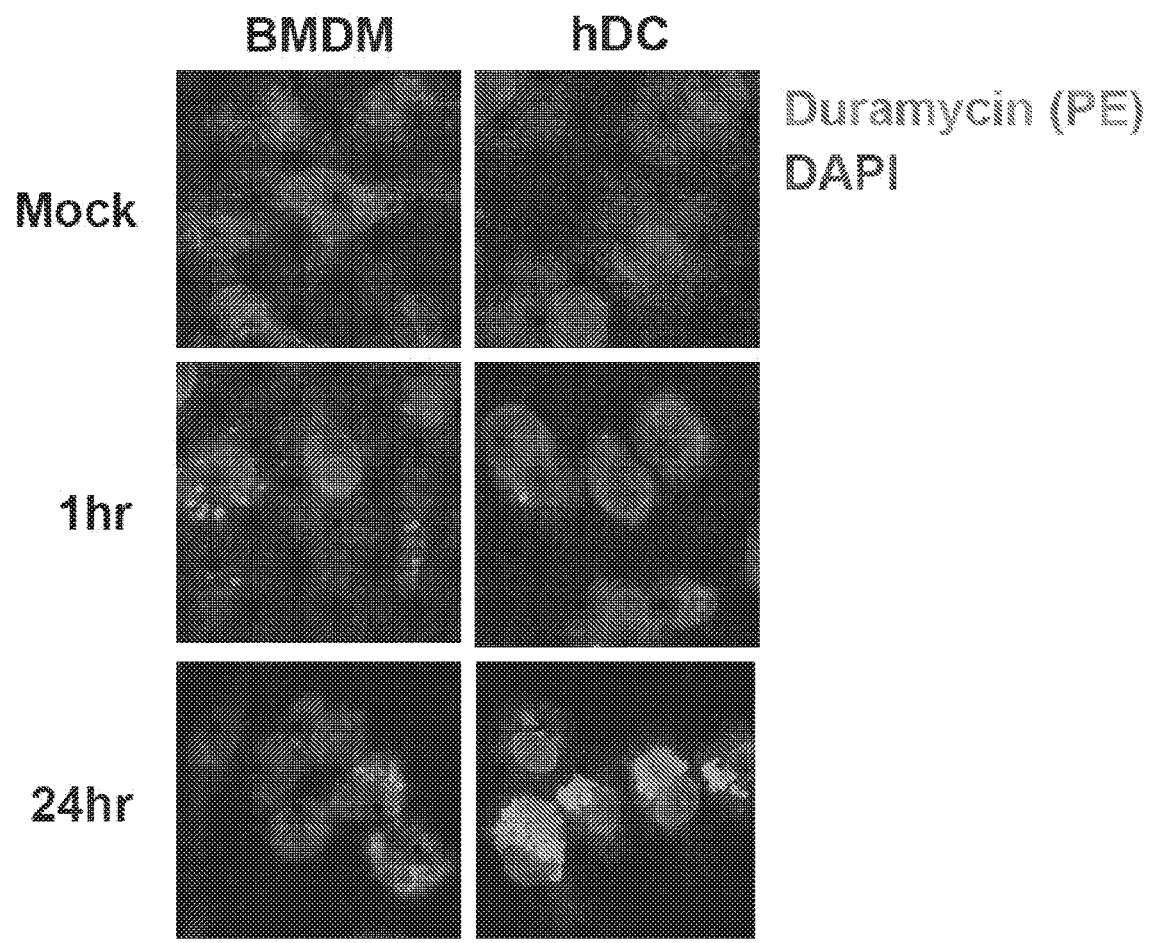
Figure 7C:
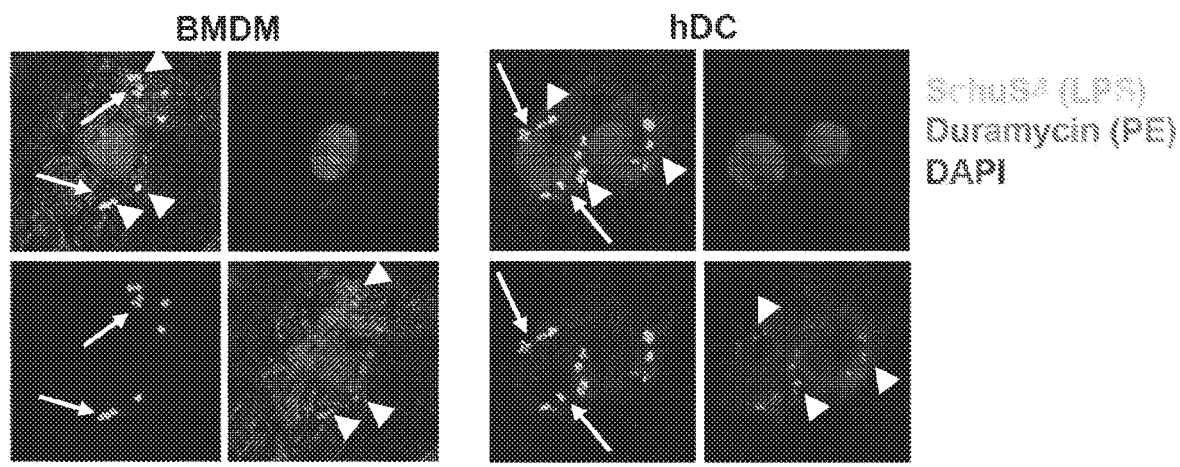

Synthetic PE 24:10, as shown below, was mixed with commercially available PC 16:18 at a ratio of 80:20 (PE:PC) and imaged by cyro-electron microscopy (FIG. 7A) to reveal lipid structure. PEPC liposomes form varied sized multilaminar structures. Bone marrow-derived macrophages (BMDM) and human dendritic cells (hDC) were treated with PEPC liposomes (FIG. 7B). At the indicated time points, the cells were fixed and stained for PE using duramycin and nuclei were counterstained with DAPI. Intracellular PEPC liposomes were detected within one hour after exposure and accumulated over a 24 hour incubation. PE is detected on the surface of viable *F. tularensis* SchuS4 (FIG. 7B). BMDM or hDC were infected with MOI=50 SchuS4 and fixed at 6 and 8 hours, respectively (FIG. 7C). Cells were stained with Alexa 488 conjugated anti-*F. tularensis* LPS antibody to detect bacteria (arrow), duramycin to detect PE (arrow head), and DAPI to detect nuclei. Colocalization of intense PE staining and SchuS4 is apparent in both BMDM and hDC from the merged in the top left image for the BMDM and hDC. Data are representative of three

Example 8. Synthetic PE:PC Liposomes Inhibit Viral Replication

Figure 10:
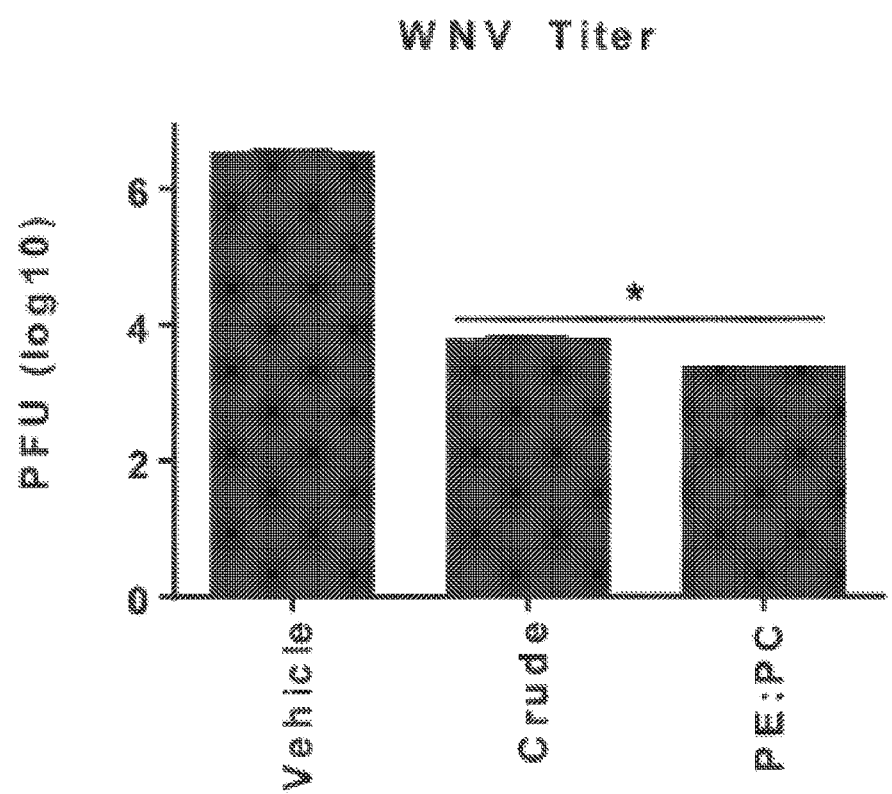

A549 human epithelial cells were treated with crude Schus4 lipid or synthetic PEPC liposomes overnight. Cells treated with 5% dextrose water served as negative controls for lipid treatment. Cells were then infected with West Nile Virus at an MOI=0.001. Forty eight hours later cells were assessed for viral load as plaque forming units (PFU) by immunostaining (FIG. 10). Error bars represent SD. $*=p<0.05$.

Example 9. Inhibition of Inflammatory Responses by PE and PC is Dependent on Acyl Chain Length BMDM were treated with crude SchuS4 lipids or the indicated PE or PC lipids or PEPC liposomes overnight. Cells were then stimulated with R848 (TLR8 agonist) and

PE(24:0, 10:0)

experiments of similar design.

Figure 8:
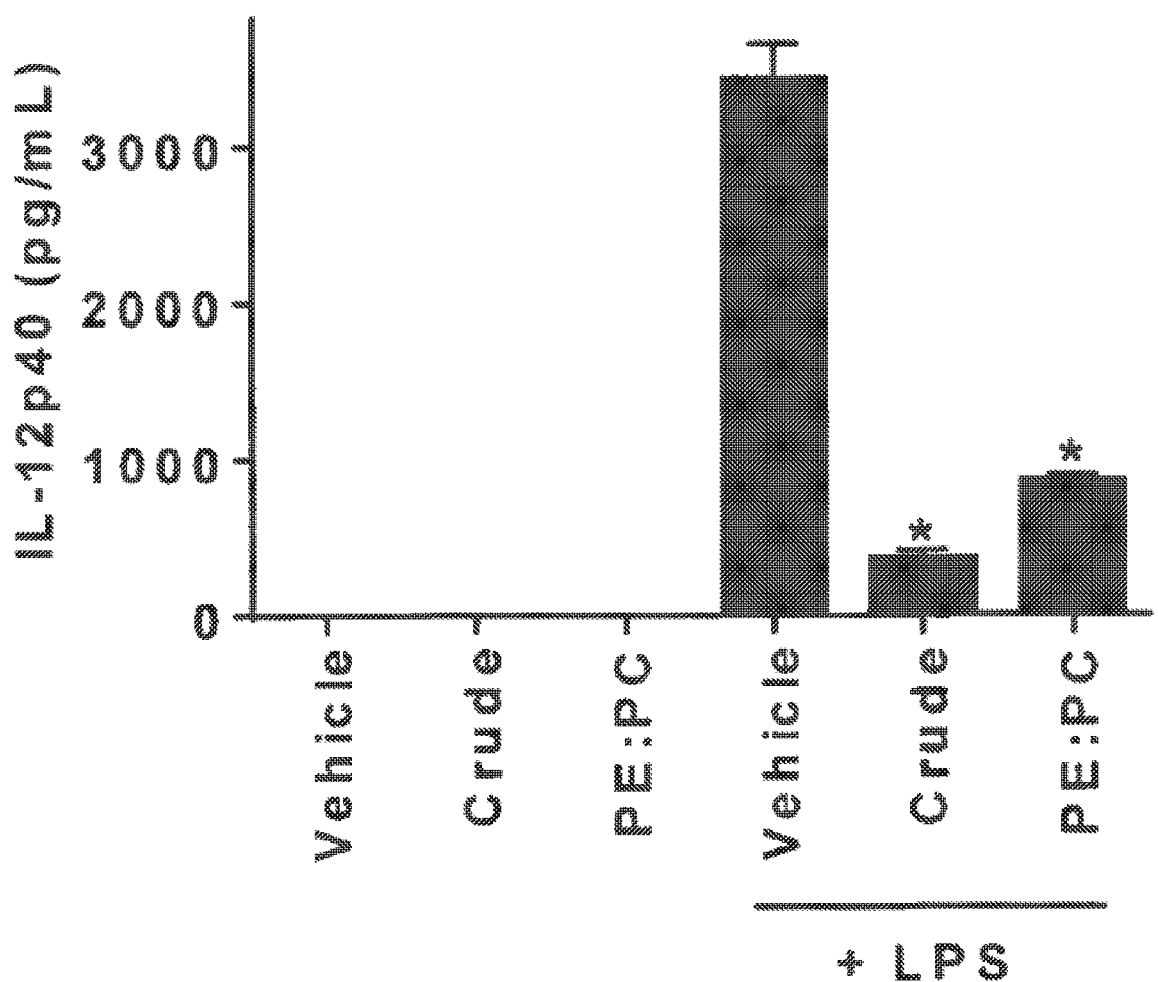

Example 6. Synthetic PE:PC Liposomes Inhibit LPS Mediated Inflammation in hDC PEPC liposomes or crude SchuS4 lipid were incubated with hDC, followed by treatment with LPS, as described with regard to FIG. 3. Cells treated with 5% dextrose water (vehicle) served as a negative control. Supernatants were evaluated for IL-12p40 by ELISA and shown in FIG. 8. Error bars represent SD and $*=p<0.05$.

Example 7. Synthetic PE:PC Liposomes Inhibit Viral Mediated Inflammation

Figure 9A:
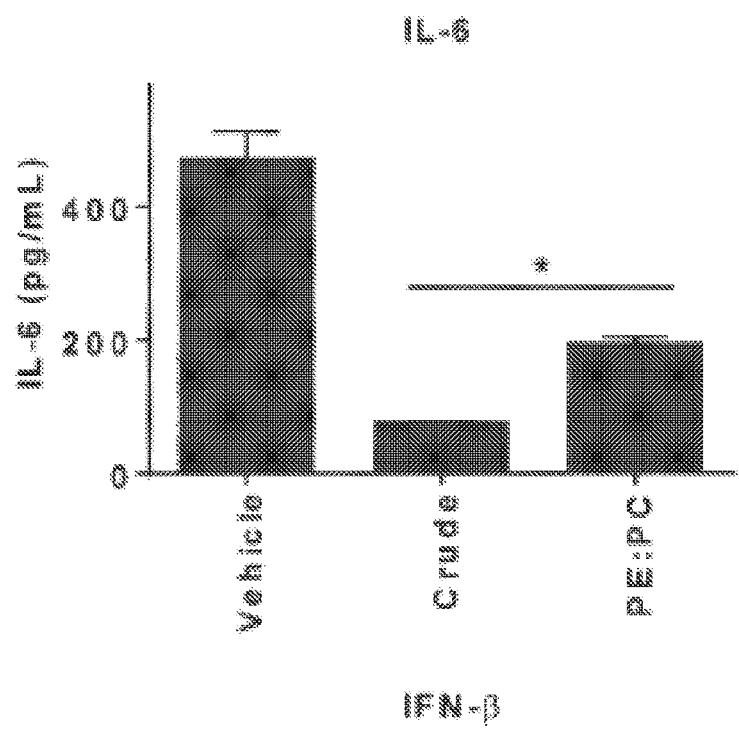
Figure 9B:
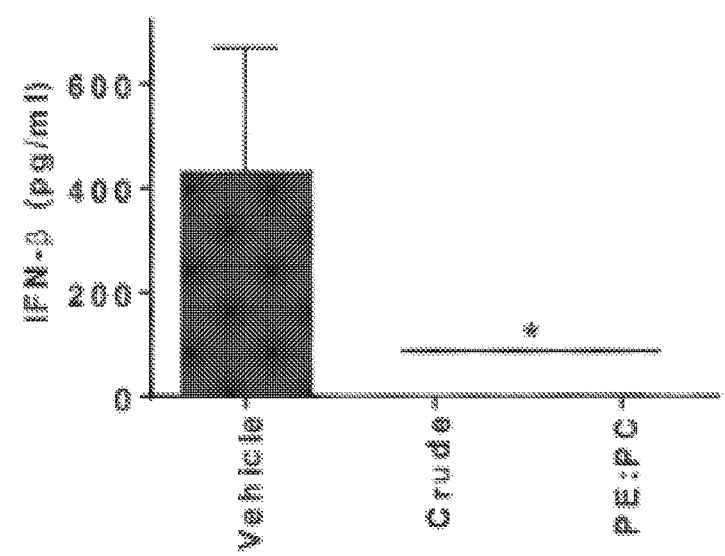
Figure 11A:
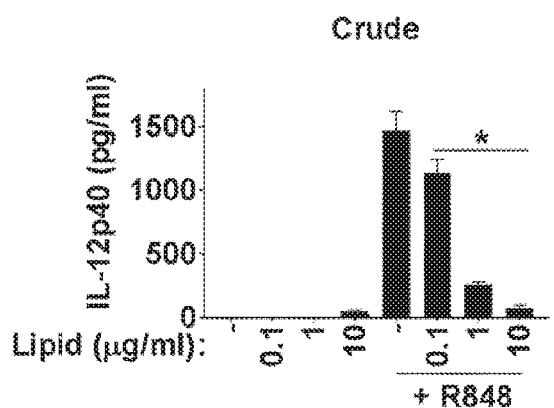
Figure 11B:
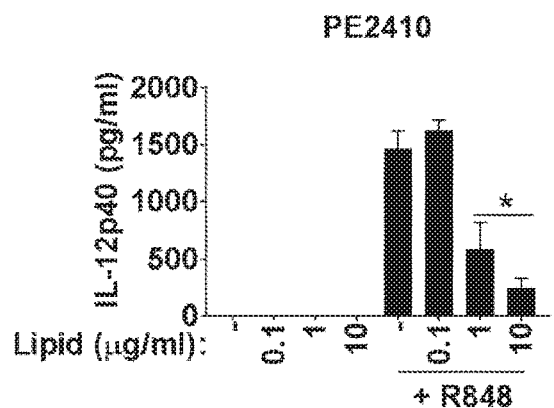
Figure 11C:
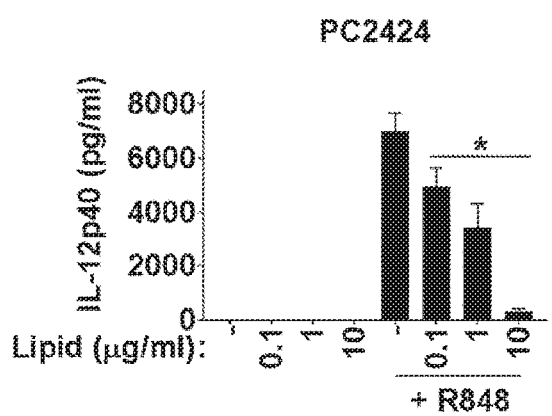
Figure 11D:
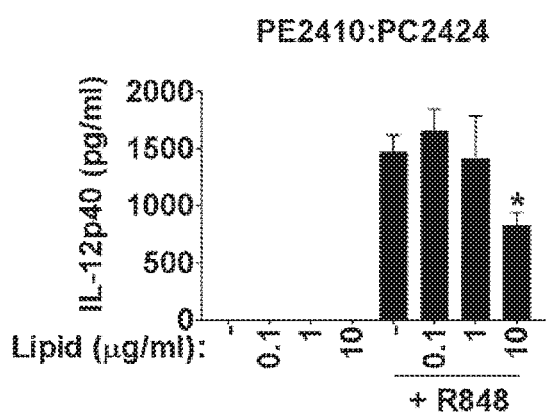
Figure 11E:
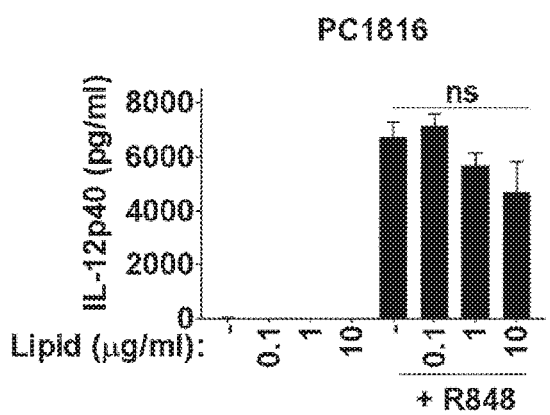
Figure 11F:
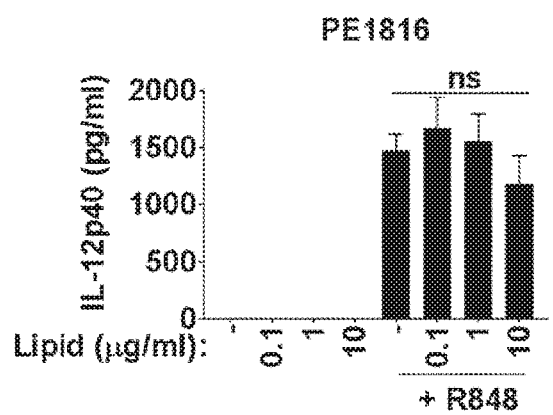

A549 human epithelial cells were treated with crude Schus4 lipid or synthetic PEPC liposomes overnight. Cells treated with 5% dextrose water served as negative controls for lipid treatment. Cells were then infected with West Nile Virus at an MOI=0.01. Forty eight hours later supernatants were collected and assessed for IL-6 (FIG. 9A) and IFN-β (FIG. 9B) by ELISA. Error bars represent SD. $*=p<0.05$.

supernatants were assessed for IL-12p40 as an indicator of induction of an inflammatory response. Crude SchuS4 lipid (FIG. 11A), PE2410 (FIG. 11B), PC2424 (FIG. 11C) and liposomes comprised of PE2410 and PC2424 (FIG. 11D) all inhibited inflammatory responses in a dose dependent manner. PC and PE lipids comprised of 1816 acyl chains did not significantly impair IL-12p40 secretion (FIGS. 11E and 11F). Error bars represent SD. $*=p<0.05$ compared to vehicle (−) control treated samples. ns=not significant. Data are representative of three experiments of similar design. Therefore, these data demonstrate that suppressive activity of PE and PC originally derived from *F. tularensis* is dependent on acyl chain length.

Material and Methods of the Examples

Generation of Bone Marrow Macrophages (BMMs).
BMMs were generated as previously described (Crane D et al. 2013, Clin Vaccine Immunol, 20:1531). Briefly, bone marrow was flushed from B6 femurs and cultured in Dulbecco's modified Eagle's medium (DMEM) (Life Technologies, Carlsbad, Calif.) supplemented with 10% heat-inactivated fetal calf serum (Atlas Biologicals, Ft. Collins, Colo.), 0.2 mM l-glutamine (Life Technologies, Carlsbad, Calif.), 1 mM HEPES buffer (Life Technologies), and 0.1 mM nonessential amino acids (Life Technologies) (cDMEM) plus 10 ng/ml macrophage colony-stimulating factor (M-CSF) (Peprotech, Rocky Hill, N.J.), in 75-cm² flasks. On day 2 of culture, non-adherent cells were collected and placed in fresh 75-cm² flasks, and the cultures were replenished with fresh cDMEM containing 10 ng/ml M-CSF. Adherent cells were collected on day 5, and seeded at $6 \times 10^4$ per well in a 96-well plate. BMMs were used on day 6 of culture.

Generation of Human Monocyte-Derived Dendritic Cells.

Human monocyte-derived dendritic cells (hDC) were generated from apheresed monocytes, as previously described (Chase, J. C., J. Celli. C. M. Bosio. 2009. Direct and indirect impairment of human dendritic cell function by virulent *Francisella tularensis* Schu S4. Infect. Immun. 77: 180-195). Briefly, monocytes were enriched by apheresis and negative selection using Dynabeads MyPure Monocytes Kit for untouched human cells, per the manufacturer's instructions (Invitrogen, Carlsbad, Calif.). Cells were differentiated upon culture in RPMI 1640 (Invitrogen) supplemented with 10% heat-inactivated FCS, 0.2 mM L-glutamine, 1 mM HEPES buffer, and 0.1 mM nonessential amino acids (all from Invitrogen) [complete RPMI (cRPMI)]; 100 ng/ml recombinant human (rh) GM-CSF; and 20 ng/ml rhIL-4 (both from PeproTech, Rocky Hill, N.J.). On day 3 of culture, cells were replenished with 100 ng/ml rhGM-CSF and 20 ng/ml rhIL-4. All cells were used on day 4 of culture. As indicated, some hDC were pretreated with 1000 U/ml rhIFN-β (PBL IFN Source, Piscataway, N.J.) 16 h prior to infection or 1-100 U/ml prior to stimulation with *Escherichia coli* LPS.

Bacteria.

*F. tularensis* strain LVS were provided by Dr. Jean Celli (Rocky Mountain Laboratories. Hamilton, Mont.) and *F. tularensis* strain SchuS4 was provided by Dr. Jeannine Peterson (Centers for Disease Control and Prevention, Fort Collins, Colo.). As previously described, bacterial stocks were generated by growing strains overnight in modified Mueller-Hinton broth, aliquoted into 1-ml samples, and frozen at −80° C. (Bosio, C. M., H. Bielefeldt-Olhmann, J. T. Belisle. 2007. Active suppression of the pulmonary immune response by *Francisella tularensis* Schu4. J. Immunol. 178: 4538-4547; Chase, J. C., J. Celli, C. M. Bosio. 2009. Direct and indirect impairment of human dendritic cell function by virulent *Francisella tularensis* Schu S4. Infect. Immun. 77: 180-195; and Nigrovic, L. E., S. L. Wingerter. 2008. Tularemia. Infect. Dis. Clin. North Am. 22: 489-504, ix). Immediately prior to infection, bacterial stocks were thawed, pelleted by centrifugation, and resuspended in cRPMI. Frozen stocks were titered by enumerating viable bacteria from serial dilutions plated on modified Mueller-Hinton agar, as previously described (Bosio, C. M., H. Bielefeldt-Ohmann. J. T. Belisle. 2007. Active suppression of the pulmonary immune response by *Francisella tularensis* Schu4. J. Immunol. 178: 4538-4547; Chase, J. C., J. Celli, C. M. Bosio. 2009. Direct and indirect impairment of human dendritic cell function by virulent *Francisella tularensis* Schu S4. Infect. Immun. 77: 180-195; and Nigrovic, L. E., S. L. Wingerter. 2008. Tularemia. Infect. Dis. Clin. North Am. 22: 489-504, ix). The number of viable bacteria in frozen stock vials varied by <1% over a 10-mo period. Where indicated, SchuS4 was killed by incubation in 2% paraformaldehyde (PFA) for 30 min at 37° C. washed extensively in PBS, and resuspended in cRPMI before addition to hDC cultures.

Infection of BMDM.

BMDM were seeded at $2 \times 10^5$ cells/well in a 24 well plate containing glass coverslips. Media was removed and reserved. Bacteria were diluted in cDMEM and added to BMDM at a multiplicity of infection (MOI) of 50. After 1.5 hours, bacteria-containing media was removed and cDMEM containing 50 µg/mL gentamicin (Life Technologies) was added for 45 minutes. Cells were then washed three times with PBS and reserved media was added back to each well. Cells were fixed at the indicated times points and coverslips removed for staining of bacteria with Alexa 488 conjugated anti-*Francisella* LSP antibody, duramycin, and DAPI as described below.

Infection of hDC.

hDC were infected at a multiplicity of infection of 50 with *F. tularensis*, as previously described (Chase, J. C., J. Celli, C. M. Bosio. 2009. Direct and indirect impairment of human dendritic cell function by virulent *Francisella tularensis* Schu S4. Infect. Immun. 77: 180-195). Briefly, hDC were removed from their original cultures, centrifuged, and adjusted to $1-2 \times 10^7$/ml in reserved DC medium. Cells treated with medium alone served as negative controls. Bacteria were added, and cells were incubated at 37° C. in 7% $CO_2$ for 2 hours, washed once, and then incubated with 50 µg/ml gentamicin (Invitrogen) for 45 min to kill extracellular bacteria. Then cells were washed extensively, adjusted to $5 \times 10^5$ cells/ml in reserved DC medium, and plated at 1 or 0.5 ml/well in 24- or 48-well tissue culture plates, respectively. Intracellular bacteria were enumerated following lysing of hDC with $H_2O$ and plating serial dilutions of cell lysate onto modified Mueller-Hinton broth agar plates. Agar plates were incubated at 37° C./7% $CO_2$ for 48 h, and individual colonies were enumerated.

Where indicated, cells were treated with 10 ng/ml ultrapure *E. coli* LPS at the same time that other cells were infected or 24 hours post infection.

Cytokine Quantification.

The presence of IL-12p40 in culture supernatants was quantified using commercially available ELISA, according to the manufacturer's instructions (R&D Systems, Minneapolis, Minn.). In experiments measuring secretion of cytokines by SchuS4-infected hDC in the presence of either mouse IgG (isotype, R&D Systems), the percentage of cytokine secretion of control (uninfected, LPS-treated cells) was calculated using the following equation (concentration of cytokine present in SchuS4-infected culture/average cytokine concentration in LPS-treated, uninfected culture)×100.

Mice.

Specific-pathogen-free, 6- to 8-week-old C57BL/6J mice (n=4 or 5/group) were purchased from Jackson Laboratories (Bar Harbor, Me.). Mice were housed in sterile microisolator cages in the biosafety level 2 facility at the Rocky Mountain Laboratories. All mice were provided sterile water and food ad libitum. All research involving animals was conducted in accordance with animal care and use guidelines, and animal protocols were approved by the animal care and use committee at Rocky Mountain Laboratories.

Isolation of Bacterial Lipids.

Lipids were isolated from SchuS4 using the standard modified Folch method for isolation of bacterial lipids (Folch J, Lees M, Sloane Stanley G H. 1957. A simple method for the isolation and purification of total lipids from animal tissues. J. Biol. Chem. 226:497-509; Beatty W L, Rhoades E R, Ullrich H J. Chattejee D, Heuser J E, Russell D G. 2000. Trafficking and release of mycobacterial lipids from infected macrophages. Traffic 1:235-247; Dunnick J K, O'Leary W M. 1970. Correlation of bacteria lipid composition with antibiotic resistance. J. Bacteriol. 101:892-900; and Liu X, Curtiss R III. 2012. Thermorecovery of cyanobacterial fatty acids at elevated temperatures. J. Biotechnol.

161:445-449). Briefly, bacteria were thawed and plated onto 150-mm petri dishes containing modified Mueller-Hinton agar. Bacteria were incubated for 48 h at 37° C. in 7% $CO_2$, scraped from the agar plates, and added to high performance liquid chromatography (HPLC)-grade chloroform/methanol (2:1) (both from Sigma). The resulting mixture was stirred vigorously for 15 min at room temperature. Then, 20 ml of endotoxin-free water was added and the mixture was stirred for an additional 10 min. The mixture was centrifuged at 4,000×g for 10 min at room temperature, to separate the organic and aqueous phases. The organic phase was pipetted into a separate container and dried under nitrogen. Dried organic samples were reconstituted in absolute ethanol (EtOH) (Warner-Graham) to 20 mg/ml. The average yield of lipids from *Francisella* was 80 mg/4 g (wet weight) of bacteria, representing approximately 2% of wet weight. Thus, 10 μg/ml of lipid is 0.00025% (wet weight) of bacteria. Lipid preparations were stored at 4° C. for up to 2 months. An absence of proteins and carbohydrates present in the organic phase was confirmed by analysis of preparations on silver-stained SDS-PAGE gels, protein quantification using the Bradford assay (Sigma) according to the manufacturer's instructions, periodate staining of SDS-PAGE gels, and Western blotting for *Francisella* O antigen and capsule. No evidence for proteins or carbohydrates was observed in organic-phase preparations.

In Vivo Assessment of Lipid Activity.

Mice were anesthetized by intraperitoneal injection of 100 μl of 12.5 mg/ml ketamine plus 3.8 mg/m xylazine. Mice were given 25 μg SchuS4 lipids in 25 μl phosphate-buffered saline (PBS) intranasally. Mice receiving EtOH alone served as negative controls for lipid-treated mice. Sixteen hours later, mice were anesthetized as described above and were given either ultrapure *E. coli* K-12 LPS (InvivoGen) or LPS derived from *E. coli* 0127:B8 (Sigma) (200 ng/25 μl). Similar results were observed regardless of which LPS type was administered to the animals. At the indicated time points, mice were euthanized. Tracheas were exposed and cannulated with disposable 18-gauge catheters. Airways were repeatedly flushed with 0.5 ml PBS. The first 0.5-ml wash from the bronchoalveolar lavage (BAL) was collected for assessment of cytokines, followed by 4 additional 0.5-ml washes to collect cells for analysis by flow cytometry.

Detection of Secreted Cytokines and Chemokines.

TNF-α, IL-6, IL-12p40, and IL-10 (all from BD Biosciences), and keratinocyte chemoattractant (KC) (R&D Systems) present in bronchoalveolar lavage fluid were quantitated using commercially available ELISA kits, following the manufacturers' instructions.

Flow Cytometry.

Populations of cells in bronchoalveolar lavage fluid were assessed by flow cytometry as described previously (Crane D D, Scott D P, Bosio C M. 2012. Generation of a convalescent model of virulent *Francisella tularensis* infection for assessment of host requirements for survival of tularemia. PLoS One 7:e33349. 10.1371/journal.pone.0033349). Briefly, the following antibodies in various combinations were used for flow cytometric analysis: PerCp/Cy5.5-CD11c, PECy7-CD11b, phycoerythrin (PE)-Ly6C, fluorescein isothiocyanate (FITC)-Ly6G, and antigen-presenting cell major histocompatibility complex II (MHC-II) (all from eBioscience. San Diego, Calif.). Neutrophils were characterized as $Ly6G^+$ $MHC\text{-}II^-$. Alveolar macrophages were characterized as $CD11c^+$ $Ly6G^-$ $Ly6C^-$ $MHC\text{-}II^-$. Staining was performed in fluorescence-activated cell sorting (FACS) buffer at room temperature. Following staining, cells were washed and fixed for 30 min in 1% paraformaldehyde at 4° C. Cells were washed a final time, resuspended in FACS buffer, and stored at 4° C. until analysis. Samples were collected using a LSRII flow cytometer (BD Biosciences). Analysis gates were set on viable unstained cells and were designed to include all viable cell populations. Approximately 10,000 gated events were analyzed for each sample. Isotype control antibodies were included when analyses were first being performed, to ensure the specificity of staining, but were not routinely included in each experiment. Data were analyzed using FlowJo software (TreeStar, Ashland, Oreg.).

Lipid Analysis.

Analytical TLC plates were from Sigma-Aldrich-Fluka and preparative TLC plates (1000μ, 20×20 cm) were from Analtech. Aminopropyl silica was from Phenomenex and silica gel solid phase extraction columns from Waters. Primuline, ninhydrin, copper sulfate, isopropanol, acetone, hexane, ethyl acetate and triglyceride standards were from Sigma-Aldrich, chloroform from Macron, methanol from Burdick Jackson. Phospholipid standards were purchased from Avanti.

Analytical TLC.

Silica gel plates were developed in chloroform:methanol: water, 7:3:0.25 for analysis of fractions I and III (see solid phase extraction below) and phosphoplipid standards. Plates were developed in hexane:diethyl ether:acetic acid, 7:3:0.1 for fraction II and fatty acid standards. Visualization of lipids was done with long wavelength U V after spraying with primuline. Phospholipids were also visualized by molybdenum blue reaction and PE by spraying with ninhydrin and heating at 115° C. for 10 to 15 minutes. $C_{18}$ silica plates were run in methanol:dichloromethane:water, 8:2:0.2 and visualization was done by charring at 120° C. after spraying with copper sulfate in phosphoric acid. PE was also visualized by ninhydrin spray on these plates.

Preparative TLC.

Crude lipid extract was dissolved in chloroform to a concentration of approximately 100 mg/ml. Typically, 10 mg of sample was applied in a narrow zone 8 cm. in length on the origin. An equal volume of pure solvent was applied in the same way adjacent to the sample. The plate was placed in ethylacetate:methanol, 3:2 and the solvent was allowed to move 0.5 cm past the origin. The plate was dried and developed with chloroform:methanol:water, 7:3:0.25. After drying the plate was sprayed with primuline and the lipid bands were visualized by fluorescence with long wavelength UV. Bands were excised with a scalpel and the silica was soaked, with mixing, in 4 ml chloroform:methanol, 1:1, for 2 hours in sealed glass vials. Approximately equal areas of silica adjacent to the sample bands were excised and processed the same way. The slurry was filtered on a fritted glass funnel and the silica was washed with 2 ml of ethyl acetate followed by 2 ml of methanol. The filtrates were combined and filtered through 0.2 micron regenerated cellulose filters and the solvent evaporated under an argon stream. The residue was stored under argon at $^-$20° C.

Fractionation by Solid Phase Extraction.

Fractionation of crude lipid into three classes was based on the method of Kaluzny (1). One milliliter of 25 mg/ml of crude lipid in chloroform was gravity loaded on a 2 gram aminopropyl silica column previously washed with 15 ml of hexane. After complete entry into the bed the hexane was eluted with brief vacuum suction. The column was sequentially developed with 14 ml of chloroform:isopmpanol, 2:1 (1), 2% acetic acid in diethylether (II) and methanol (III). The three fractions were dried under argon and stored at $^-$20° C. Further fractionation of the phospholipid class was based on the method of Fauland (2) with modifications. Approximately 10 mg of fraction III dissolved in 10 ml of chloroform:methanol, 2:1, was loaded on to a 1 gram silica extraction column washed in the same solvent. Another 10 ml of solvent was applied to the column. Fractions were collected throughout the loading and washing. Ten milliliters of chloroform:methanol, 1.5:1, was applied and fractions were collected. The column was then washed with 10 ml of methanol which was collected in two fractions. The fractions were dried under argon, dissolved chloroform:methanol, 1:1, and analyzed by TLC. Primuline fluorescence revealed the majority of PE was eluted and a single spot in the first 25 ml. All these fractions were also ninhydrin positive. PC appeared as a single spot in the methanol fractions. Both lipid fractions were pooled separately and dried.

Separation of Phospholipid Molecular Species by HPLC.

Chromatography was done at 0.3 mL/min on a 2.0 mm×100 mm $C_{18}$ Luna column (Phenomenex) in 94% methanol:acetonitrile, 4:1, 6% water. A 1260 Agilent analytical HPLC was used and detection was done at 208 nm. Dried, pooled PE and PC silica fractions were dissolved in 0.25 mL chloroform:methanol, 1:1. Aliquots of 25 µl to 50 µl were diluted with 4 parts methanol, injected and fractions collected. Typical runs were 60 minutes for PE and 80 minutes for PC in order to elute a highly retained component. Under these conditions $PE(C_{10:0})_2$ and $PE(C_{14:0})_2$ eluted at 7 and 10 minutes respectively. $PE(C_{16:0})_2$ eluted at 22 minutes and $PE(C_{18:1})_2$ at 25 minutes. $PE(1-C_{24:0}, 2-C_{10:0}-)$ eluted at approximately 50 minutes. Peaks were broad and asymmetric. The S4 PE was resolved into four major peaks and the PC into six.

Preparation of Virus Stocks and Assessment of Viral Load.

Stocks of West Nile Virus were generated following infection of VERO cells cultured in DMEM supplemented with 10% heat inactivated fetal bovine serum. Cell culture supernatants were collected and centrifuged at 100,000×g at 4° C. and were stored at ⁻80° C. Virus titers in A549 cells were enumerated as previously described (Beaty B. J., Calisher C. H., Shope R. S. 1989) Arboviruses. in Diagnostic procedures for viral, rickettsial and chalmydial infections. eds Schmidt N. J., Emmons R. W. [American Public Health Association, Washington, D.C.] pp 797-856).

Statistical Analysis.

Statistical differences between two groups were determined using an unpaired t test, with significance set at P<0.05. For comparisons of three or more groups, analysis was done by one-way analysis of variance (ANOVA) followed by Tukey's multiple-comparisons test, with significance determined at P<0.05.

Specific Embodiments

According to an aspect, the present disclosure provides an anti-inflammatory composition comprising: an effective amount of purified lipid from *Francisella tularensis* or modified form thereof.

In any aspect or embodiment described herein, the *Francisella tularensis* is a virulent strain.

In any aspect or embodiment described herein, the purified lipid comprises a phosphatidylethanolamine (PE).

In any aspect or embodiment described herein, the purified lipid is enriched for the PE.

In any aspect or embodiment described herein, the purified lipid is PE.

In any aspect or embodiment described herein, the composition further comprises phosphatidylcholine (PC).

In any aspect or embodiment described herein, the PE, and/or the PC comprises an acyl chain with a length in a range of from 5 to 13 or from 20 to 28 carbons.

In any aspect or embodiment described herein, the PE and/or the PC comprises two acyl chains, wherein at least one chain has a length in the range of from 5 to 13 carbons.

In any aspect or embodiment described herein, the PE and/or the PC comprises two acyl chains, wherein at least one chain has a length in the range of from 20 to 28 carbons.

In any aspect or embodiment described herein, the PE and/or the PC comprises two acyl chains, wherein one chain has a length in the range of from 5 to 13 carbons and the other chain has a length in the range of from 20 to 28 carbons.

In any aspect or embodiment described herein, the ratio of PE:PC is in a range of from about 50:50 to about 95:5.

In any aspect or embodiment described herein, the composition further comprises another purified lipid from *Francisella tularensis*.

In any aspect or embodiment described herein, the composition is a liposome.

In any aspect or embodiment described herein, the composition is an emulsified liposome.

In any aspect or embodiment described herein, the liposome has a diameter in a range of from about 20 nm to about 1,500 nm.

According to another aspect, the present disclosure provides a liposome comprising: purified lipid from *Francisella tularensis* or modified form thereof.

In any aspect or embodiment described herein, the *Francisella tularensis* is a virulent strain.

In any aspect or embodiment described herein, the purified lipid comprises a phosphatidylethanolamine (PE).

In any aspect or embodiment described herein, the purified lipid is enriched for the PE.

In any aspect or embodiment described herein, the purified lipid is PE.

In any aspect or embodiment described herein, the liposome further comprises phosphatidylcholine (PC).

In any aspect or embodiment described herein, the PE and/or the PC comprises an acyl chain with a length in a range of from 5 to 13 or from 20 to 28 carbons.

In any aspect or embodiment described herein, the PE and/or the PC two acyl chains, wherein at least one chain has a length in the range of from 5 to 13 carbons.

In any aspect or embodiment described herein, the PE and/or the PC comprises two acyl chains, wherein at least one chain has a length in a range of from 20 to 28 carbons.

In any aspect or embodiment described herein, the PE and/or the PC comprises two acyl chains, wherein one chain has a length in a range of from 5 to 13 carbons, and the other chain has a length in a range of from 20 to 28 carbons.

In any aspect or embodiment described herein, the ratio of PE:PC is in a range of from about 50:50 to about 95:5.

In any aspect or embodiment described herein, the liposome further comprises another purified lipid from *Francisella tularensis*.

In any aspect or embodiment described herein, the liposome is an emulsified liposome.

In any aspect or embodiment described herein, the composition is a liposome or an emulsified liposome.

In any aspect or embodiment described herein, the liposome has a diameter in a range of from about 20 nm to about 1,500 nm.

According to a further aspect, the present disclosure provides an anti-inflammatory composition comprising an effective amount of a synthetic PE or modified form thereof, wherein the PE comprises two acyl chains, wherein at least one chain has a length in the range of from 5 to 13 carbons and at least one chain has a length in the range of from 20 to 28 carbons.

According to yet another aspect, the present disclosure provides an anti-inflammatory composition produced by the following process: adding virulent *Francisella tularensis* to a mixture of chloroform/methanol and mixing; adding water to the bacterial-chloroform/methanol mixture; separating the organic phase and aqueous phase; drying the organic phase, and reconstituting the dried organic phase.

In any aspect or embodiment described herein, the chloroform/methanol is at a ratio of about 3:1 to about 1:1 (such as, about 2:1).

In any aspect or embodiment described herein, the dried organic phase is reconstituted in ethanol.

In any aspect or embodiment described herein, the process further comprises isolating a band of the reconstituted organic phase that runs near the solvent front on thin layer chromatography.

In any aspect or embodiment described herein, the reconstituted dried organic phase or isolated lipid is enriched for PE.

In any aspect or embodiment described herein, the process further comprising adding PC to the isolated lipid of the reconstituted organic phase or the isolated lipid.

In any aspect or embodiment described herein, the PE and/or the PC comprises an acyl chain with a length in a range of from 5 to 13 or from 20 to 28 carbons.

In any aspect or embodiment described herein, the PE and/or the PC comprises two acyl chains, wherein at least one has a length in a range of from 5 to 13 carbons.

In any aspect or embodiment described herein, the PE and/or the PC comprises two acyl chains, wherein at least one has a length in a range of from 20 to 28 carbons.

In any aspect or embodiment described herein, the PE and/or the PC comprises two acyl chains, wherein one chain has a length in the range of from 5 to 13 carbons and the other chain has a length in the range of 20 to 28 carbons.

In any aspect or embodiment described herein, a ratio of the reconstituted organic phase or isolated lipid to PC is in a range of from about 50:50 to about 95:5.

In any aspect or embodiment described herein, the process further comprises adding another purified lipid from *Francisella tularensis*.

In any aspect or embodiment described herein, the process further comprises producing a liposome from the reconstituted organic phase, isolated lipid, or isolated lipid-PC mixture.

In any aspect or embodiment described herein, the liposome is an emulsified liposome.

In any aspect or embodiment described herein, the liposome has a diameter in a range of from about 20 nm to about 1,500 nm.

According to yet a further aspect, the present disclosure provides a pharmaceutical composition comprising a pharmaceutically effective amount of the composition of the present disclosure, or the liposome of the present disclosure.

In any aspect or embodiment described herein, pharmaceutical composition further comprises a pharmaceutically acceptable carrier.

In any aspect or embodiment described herein, the pharmaceutically acceptable carrier is a gel or cream.

According to an additional aspect a method of treating or preventing a microbial infection or inflammation resulting from a microbial infection in a patient in the need thereof, the method comprising administering an effective amount of the composition of the present disclosure, or the liposome of the present disclosure, wherein the composition or liposome is effective in treating or preventing the microbial infection or the microbial infection related inflammation.

In any aspect or embodiment described herein, the microbial infection is a bacterial or a viral infection.

In any aspect or embodiment described herein, the bacterial infection or viral infection causes dermatological inflammation and/or respiratory inflammation.

In any aspect or embodiment described herein, the bacterial infection or viral infection is selected from the group consisting of *Staphylococcus aureus, Streptococcus pyogenes, Clostridium perfringens, Bacillus anthracis, Francisella tularensis, Corynebacterium diphtheria. Streptococcus pneumoniae, Haemophilus influenza, Bordetella pertussis, Mycobacterium tuberculosis* or *bovis, Mycoplasma pneumoniae, Legionella pneumophila, Chlamydia psittaci, Chlamydia pneumoniae, Coxiella burnetii*, measles, rubella, varicella zoster, parvovirus, herpes simplex virus 6, herpes simplex virus 7, herpes simplex virus 8, Epstein Barr virus, enterovirus, coxsackie virus, togavirus, coronavirus, rhinovirus, bunyavirus, arenavirus, smallpox, cowpox, monkey pox, zika virus, dengue virus, nairovirus, arenavirus, filovirus, west nile virus, molluscum contagiosm, human papillomavirus, coronavirus, rhinovirus, respiratory syncytial virus, and Influenzavirus.

In any aspect or embodiment described herein, the composition or the liposome is administered prior to exposure to the microbial infection.

In any aspect or embodiment described herein, the composition of the liposome is administered post exposure to the microbial infection.

In any aspect or embodiment described herein, the method further comprises co-administering one or more additional therapeutic agent.

According to an aspect, the present disclosure provides a method of treating or preventing inflammation in a patient in the need thereof, the method comprising administering an effective amount of the composition of the present disclosure, or the liposome of the present disclosure to the patient, wherein the composition or liposome is effective at treating or preventing inflammation.

In any aspect or embodiment described herein, the inflammation is related to a bacterial infection, a viral infection, an autoimmune disease or disorder, and/or an allergy.

According to yet a further aspect, the present disclosure provides a method of modulating an immune response in a patient comprising administering an effective amount of the composition of the present disclosure, or the liposome of the present disclosure to the patient, wherein the composition or liposome is effective at modulating the immune response.

In any aspect or embodiment described herein, the modulation comprises enhancing the immunocompetence in the subject.

In any aspect or embodiment described herein, the modulation comprises inhibiting bacterial replication in the subject.

In any aspect or embodiment described herein, the modulation comprises inhibiting viral replication in the subject.

In any aspect or embodiment described herein, the bacterial infection or viral infection is a respiratory infection.

In any aspect or embodiment described herein, the bacterial infection or viral infection is a dermatological infection.

In any aspect or embodiment described herein, the inflammation is caused by an autoimmune disease or disorder, and/or an allergy.

In any aspect or embodiment described herein, the subject has dermatological or respiratory inflammation.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A liposome comprising:
   a synthetic phosphatidylethanolamine (PE) comprising two acyl chains, wherein one acyl chain has a length of 10 carbons and one acyl chain has a length of 24 carbons; and
   a synthetic phosphatidylcholine (PC) comprising two acyl chains, wherein both acyl chains have a length of 24 carbons
   wherein the ratio of PE:PC in the liposome is in a range from about 50:50 to about 95:5, and wherein the liposome comprises anti-inflammatory properties that inhibit inflammation resulting from a microbial infection.

2. The liposome of claim 1, wherein the ratio of PE:PC is about 80:20.

3. The liposome of claim 1, wherein the liposome is an emulsified liposome.

4. The liposome of claim 3, wherein the liposome has a diameter in a range of from about 20 nm to about 1,500 nm.

5. A pharmaceutical composition comprising a pharmaceutically effective amount of the liposome of claim 1.

6. The pharmaceutical composition of claim 5, further comprising a pharmaceutically acceptable carrier.

7. The pharmaceutical composition of claim 6, wherein the pharmaceutically acceptable carrier is a gel or cream.

8. A method of treating or inhibiting a bacterial infection or inflammation resulting from a bacterial infection in a patient in need thereof, the method comprising administering an effective amount of the liposome of claim 1.

9. A method of treating or inhibiting inflammation in a patient in need thereof, wherein the inflammation is related to a bacterial infection, the method comprising administering an effective amount of the liposome of claim 1 to the patient.

10. A liposome consisting essentially of:
    a synthetic PE comprising two acyl chains, wherein one acyl chain has a length of 10 carbons and one acyl chain has a length of 24 carbons, and a synthetic phosphatidylcholine (PC) comprising two acyl chains, wherein both acyl chains have a length of 24 carbons,
    wherein the ratio of PE:PC in the liposome is in a range from about 50:50 to about 95:5, and wherein the liposome comprises anti-inflammatory properties that inhibit inflammation resulting from a microbial infection.

11. An anti-inflammatory composition comprising an effective amount of the liposome of claim 10 and a pharmaceutically acceptable carrier or excipient.

12. A liposome consisting of:
    a synthetic PE comprising two acyl chains, wherein one acyl chain has a length of 10 carbons and one acyl chain has a length of 24 carbons, and a synthetic phosphatidylcholine (PC) comprising two acyl chains, wherein both acyl chains have a length of 24 carbons,
    wherein the ratio of PE:PC in the liposome is in a range from about 50:50 to about 95:5, and wherein the liposome comprises anti-inflammatory properties that inhibit inflammation resulting from a microbial infection.

13. An anti-inflammatory composition comprising an effective amount of the liposome of claim 12 and a pharmaceutically acceptable carrier or excipient.

14. The liposome of claim 12, wherein the ratio of PE:PC is about 80:20.

15. The liposome of claim 10, wherein the ratio of PE:PC is about 80:20.

* * * * *